United States Patent [19]

Arnold et al.

[11] Patent Number: 5,240,940

[45] Date of Patent: Aug. 31, 1993

[54] QUINOLINE AND CINNOLINE FUNGICIDE COMPOSITIONS

[75] Inventors: Wendell R. Arnold, Carmel; Michael J. Coghlan, Indianapolis; Glen P. Jourdan, Morristown; Eriks V. Krumkalns, Indianapolis; Robert G. Suhr, Greenfield, all of Ind.

[73] Assignee: DowElanco, Indianapolis, Ind.

[21] Appl. No.: 881,957

[22] Filed: May 12, 1992

Related U.S. Application Data

[60] Division of Ser. No. 334,422, Apr. 7, 1989, Pat. No. 5,145,843, which is a continuation-in-part of Ser. No. 150,266, Jan. 29, 1988, abandoned.

[51] Int. Cl.$^5$ .................... A01N 43/42; A01N 43/5o; A01N 43/64; A01N 55/00
[52] U.S. Cl. ..................... 514/312; 514/63; 514/228.8; 514/231.2; 514/239.5; 514/248; 514/255; 514/313; 514/314; 514/383; 514/388; 514/398; 514/399; 514/400; 514/525; 514/491
[58] Field of Search ............... 514/63, 248, 312, 313, 514/314, 231.2, 255, 383, 399, 491, 229, 239.5, 388, 398, 400, 525

[56] References Cited

U.S. PATENT DOCUMENTS 4,233,305  11/1980  Allais et al. ................ 514/313

Primary Examiner—Allen J. Robinson
Attorney, Agent, or Firm—Donald R. Stuart

[57] ABSTRACT

Fungicidal compositions comprise a combination of two fungicides, one of which is a quinoline or cinnoline compound of the formula (1)

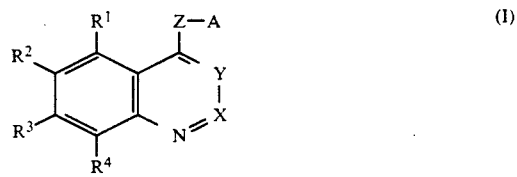

the substituents being as described in the specification.

21 Claims, No Drawings

QUINOLINE AND CINNOLINE FUNGICIDE COMPOSITIONS

This application is a division of application Ser. No. 07/334,422, filed Apr. 7, 1989, now U.S. Pat. No. 5,145,843, which is a continuation in part of Ser. No. 07/150,266, filed Jan. 29, 1988, now abandoned.

RELATED APPLICATIONS

This application is a continuation-in-part of Ser. No 07/150,266 filed Jan. 29, 1988.

BACKGROUND OF THE INVENTION

This invention provides new compounds that have excellent plant fungicide activity. Some of the compounds have also demonstrated insecticidal and miticidal activity. The invention also provides compositions and combination products that contain a compound of the invention as active ingredient. Some of the combination products have shown synergistic activity against plant pathogens. The invention also provides fungicidal methods.

There is an acute need for new fungicides, because target pathogens are rapidly developing resistance to known fungicides. Widespread failure of N-substituted azole fungicides to control barley mildew was observed in 1983, and has been attributed to the development of resistance. The field performance of DMI (demethylation inhibitor) fungicides, which are now widely relied on to protect cereal crops from powdery mildew, has declined since they were introduced in the 1970's. Similarly, the pathogen population responsible for grape Botrytis, the number one disease in grapes as well as in berry crops and in tomato and cucumber greenhouse crops, has shifted to strains that are resistant to benzimidazole and dicarboximide fungicides.

SUMMARY OF THE INVENTION

This invention provides a fungicidal method which comprises applying to the locus of the fungus a fungicidally effective amount of a compound of the formula (1)

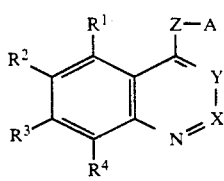

(1)

wherein
X is $CR^5$ or N, where $R^5$ is H, Cl, or $CH_3$;
Y is $CR^{5'}$ wherein $R^{5'}$ is H, Cl, or Br;
Z is O, S, SO, $SO_2$, $NR^6$, where $R^6$ is H, $(C_1-C_4)$ alkyl, or $(C_1-C_4)$ acyl, or $CR^7R^8$, where $R^7$ and $R^8$ are independently H, $(C_1-C_4)$ acyl, $(C_1-C_4)$ alkyl, $(C_1-C_4)$ alkenyl, $(C_2-C_4)$ alkynyl, CN, or OH, or $R^7$ and $R^8$ combine to form a carbocyclic ring containing four to six carbon atoms;
$R^1$ to $R^4$ are independently H, OH, $NO_2$, halo, I, $(C_1-C_4)$ alkyl, $(C_3-C_4)$ branched alkyl, $(C_1-C_4)$ alkoxy, halo $(C_1-C_4)$ alkyl, halo $(C_1-C_4)$ alkoxy, or halo $(C_1-C_4)$ alkylthio; or $R^1$ and $R^2$ or $R^2$ and $R^3$ combine to form a carbocyclic ring containing 4 to 6 carbon atoms;
A is
(a) a $C_1-C_{18}$ saturated or unsaturated hydrocarbon chain, straight chain or branched, optionally including a hetero atom selected from O, S, SO, $SO_2$, or Si, and optionally substituted with halo, halo $(C_1-C_4)$ alkoxy, hydroxy, or $(C_1-C_4)$ acyl;
(b) $(C_3-C_8)$ cycloalkyl or cycloalkenyl;
(c) a phenyl group of the formula (2)

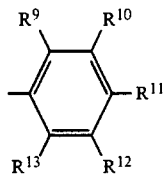

(2)

wherein $R^9$ to $R^{13}$ are independently
H,
CN,
$NO_2$,
OH,
halo,
I,
$(C_1-C_4)$ alkyl,
$(C_3-C_4)$ branched alkyl,
$(C_2-C_4)$ acyl,
halo $(C_1-C_7)$ alkyl,
hydroxy $(C_1-C_7)$ alkyl,
$(C_1-C_7)$ alkoxy,
halo $(C_1-C_7)$ alkoxy,
$(C_1-C_7)$ alkylthio,
halo $(C_1-C_7)$ alkylthio,
phenyl,
substituted phenyl,
phenoxy,
substituted phenoxy,
phenylthio,
substituted phenylthio,
phenyl $(C_1-C_4)$ alkyl,
substituted phenyl $(C_1-C_4)$ alkyl,
benzoyl,
substituted benzoyl,
$SiR^{20}R^{21}R^{22}$ or $OSiR^{20}R^{21}R^{22}$, where $R^{20}$, $R^{21}$, and $R^{22}$ are H, a $C_1-C_6$alkyl group, straight chain or branched, phenyl, or substituted phenyl, provided that at least one of $R^{20}$, $R^{21}$, and $R^{22}$ is other than H, or $R^{11}$ and $R^{12}$ or $R^{12}$ and $R^{13}$ combine to form a carbocyclic ring, provided that unless all of $R^9$ to $R^{13}$ are H or F, then at least two of $R^9$ to $R^{13}$ are H;
(d) a furyl group of formula (3)

(3)

wherein $R^{14}$ is H, halo, halomethyl, CN, $NO_2$, $(C_1-C_4)$ alkyl, $(C_3-C_4)$ branched alkyl, phenyl, or $(C_1-C_4)$ alkoxy,
(e) a thienyl group of formula (4)

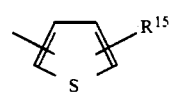

(4)

wherein $R^{15}$ is H, halo, halomethyl, CN, $NO_2$, $(C_1-C_4)$ alkyl, $(C_3-C_4)$ branched alkyl, phenyl, or $(C_1-C_4)$ alkoxy, (f) a group of formula (5) or (5a)

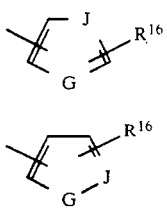

(5)

(5a)

wherein $R^{16}$ is H, halo, halomethyl, CN, $NO_2$, $(C_1-C_4)$ alkyl, $(C_3-C_4)$ branched alkyl, phenyl, substituted phenyl, or $(C_1-C_4)$ alkoxy, and J is N or CH and G is O, $NR^{19}$ or CH, provided that either J is N or G is $NR^{19}$, where $R^{19}$ is H, $(C_1-C_4)$ alkyl, $(C_1-C_4)$ acyl, phenylsulfonyl, or substituted phenylsulfonyl;

(g) a group selected from
1-naphthyl,
substituted 1-naphthyl,
4-pyrazolyl,
3-methyl-4-pyrazolyl,
1,3-benzodioxolyl,
tricyclo[3.3.1.1(3,7)]dec-2-yl,
1-(3-chlorophenyl)-1H-tetrazol-5-yl,
pyridyl,
substituted pyridyl,
pyridazinyl, or an acid addition salt of a compound of formula (1), or an N-oxide of a compound of formula (1) where Y is CH; provided Z is $CR^7R^8$ if A is a group described in paragraph (d), (e), or (f); and provided that Z is S, SO, or $SO_2$ if A is a group described in paragraph (a).

The invention also provides novel compounds of formula (1), as defined above
provided that the following additional compounds are excluded:

1) compounds wherein Z is O, X and Y are both CH, $R^3$ is Cl, the rest of $R^1$ to $R^4$ are H, and A is phenyl, 4-chlorophenyl, or 4-fluorophenyl; and 2) compounds wherein X and Y are both CH, $R^1$ to $R^4$ are H, or $R^1$, $R^3$, and $R^4$ are H and $R^2$ is F, $R^5$ is $CH_3$, and Z is O;

3) compounds wherein A is unsubstituted phenyl and $R^1$ to $R^4$ are all H or $R^2$ is $NO_2$ and the rest of $R^1$ to $R^4$ are H;

4) 7-chloro-4-[3-(trifluoromethyl)phenoxy]-quinoline;

5) 6-fluoro-2-methyl-4-[2-nitro-4-(trifluoromethyl)-phenoxy]quinoline;

6) 7-chloro-4-(4-chloro-3,5-dimethylphenoxy)-quinoline;

7) 7-chloro-4-(4-chloro-3-methylphenoxy)-quinoline;

8) 5-chloro-4-[2,6-dinitro-4-(trifluoromethyl)phenoxy]-2,8-dimethylquinoline;

9) 8-chloro-2-methyl-4-[2-nitro-4-(trifluoromethyl)-phenoxy]quinoline;

10) compounds wherein Z is $NR^6$.

The fungicidal combinations of the invention comprise at least 1% by weight of a compound of formula (1), or an acid addition salt of a compound of formula (1) or an N-oxide of a compound of formula (1) where Y is CH, in combination with a second fungicidal compound.

The fungicidal compositions of the invention comprise a compound of formula (1), or an acid addition salt of a compound of formula (I) or an N-oxide of a compound of formula (1) where Y is CH, in combination with a phytologically-acceptable carrier.

DETAILED DESCRIPTION OF THE INVENTION

Throughout this document, all temperatures are given in degrees Celsius, and all percentages are weight percentages unless otherwise stated.

The term halo, used alone or in combination with other terms, such as alkyl or alkoxy, refers to F, Cl, or Br.

The term "$(C_1-C_4)$ alkyl" refers to straight chain alkyl radicals.

The term "branched $(C_3-C_4)$ alkyl" refers to all alkyl isomers containing the designated number of carbon atoms, except the straight chain isomers.

The term "$(C_1-C_7)$ alkoxy" refers to straight or branched chain alkoxy groups.

The term "halo $(C_1-C_7)$ alkyl" refers to a $(C_1-C_7)$ alkyl group, straight chain or branched, substituted with one or more halo atoms.

The term "halo $(C_1-C_7)$ alkoxy" refers to a $(C_1-C_7)$ alkoxy group, substituted with one or more halo atoms.

The term "halo $(C_1-C_7)$ alkylthio" refers to a $(C_1-C_7)$ alkylthio group, straight chain or branched, substituted with one or more halo groups.

The term "$(C_1-C_4)$ acyl" refers to straight chain or branched acyl groups.

The term "substituted phenyl" refers to phenyl substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The term "substituted phenoxy" refers to phenoxy substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The term "substituted phenylthio" refers to a phenylthio group substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The term "substituted phenylsulfonyl" refers to a phenylsulfonyl group substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The term "unsaturated hydrocarbon chain" means a hydrocarbon chain containing one to three multiple bond sites.

The term "carbocyclic ring" refers to a saturated or unsaturated ring of four to seven carbon atoms.

"HPLC" refers to high-performance liquid chromatography.

Compounds

While all of the compounds of the invention are useful fungicides, certain classes are preferred for reasons of greater efficacy or ease of synthesis, viz:

1) Compounds of formula (1) where at least two of $R^1$ to $R^4$ are H;

2) Compounds of preferred class (1) wherein three of $R^1$ to $R^4$ are hydrogen, and one is other than hydrogen;

3) Compounds of preferred class 2 wherein $R^3$ is Cl and the rest of $R^1$ to $R^4$ are H;

4) Compounds of preferred class 2 wherein $R^4$ is Cl and the rest of $R^1$ to $R^4$ are H;

5) Compounds of preferred class 1 wherein $R^1$ and $R^3$ are both Cl or both $CH_3$ and the rest of $R^1$ to $R^4$ are H;

5a) Compounds of preferred class 5 wherein A is unsubstituted phenyl;

6) Compounds of formula (1) wherein A is substituted phenyl;

7) Compounds of preferred class 6 wherein $R^{11}$ is F;

8) Compounds of preferred class 6 wherein A is phenyl ortho-substituted with an electron-withdrawing group;

9) Compounds of preferred class 8 wherein $R^9$ is halo, $CF_3$, CN, or $NO_2$;

10) Compounds of formula (1) wherein X and Y are CH and Z is O (i.e., 4-quinolinyl ethers);

11) Compounds of preferred class 10 wherein $R^3$ is Cl and the rest of $R^1$ to $R^4$ are H (i.e., 7-chloro-4-quinolinyl ethers);

12) Compounds of the preferred class 10 wherein $R^3$ is Br and the rest of $R^1$ to $R^4$ are H (i.e., 7-bromo-4-quinolinyl ethers);

13) Compounds of preferred class 10 wherein $R^1$ and $R^3$ are Cl and the rest of $R^1$ to $R^4$ are H (i.e., 5,7-dichloro-4-quinolinyl ethers);

14) Compounds of preferred class 10 wherein $R^4$ is Cl and the rest of $R^1$ to $R^4$ are H (i.e., 8-chloro-4-quinolinyl ethers);

15) Compounds of preferred class 10 wherein A is 4-fluorophenyl;

16) Compounds of preferred class 10 wherein A is phenyl ortho-substituted with an electron withdrawing group;

For curative as well as protective powdery mildew control, compounds of formula (1) wherein X and Y are CH, Z is O, and $R^3$ is Cl (i.e., 7-chloro-4-quinolinyl ethers) are especially preferred, and most preferred within this class are 7-chloro-4-(4-fluorophenoxy)-quinoline (a compound not claimed per se, but, included in the claimed methods and compositions), 7-chloro-4-(2-nitrophenoxy)-quinoline, 4-(2-bromophenoxy)-7-chloroquinoline, 7-chloro-4-(2-chlorophenoxy)quinoline, 2-[(7-chloro-4-quinolinyl)-oxy]benzonitrile, 7-chloro-4-(2,4-difluorophenoxy)quinoline, 7-chloro-4-(2-cyanophenoxy)quinoline, and 7-chloro-4-[-2(trifluoromethyl)phenoxy]quinoline.

For protective, as well as some curative powdery mildew control, compounds of formula (1) wherein X and Y are CH, Z is O, and $R^1$ and $R^3$ are Cl or $CH_3$ (i.e., 5,7-dichloro-4-quinolinyl ethers and 5,7-dimethyl-4-quinolinyl ethers) are especially preferred. Most preferred within this class are 5,7-dichloro-4-(4-fluorophenoxy)quinoline, 5,7-dichloro-4-(4-fluorophenoxy)-quinoline, hydrochloride, 5,7-dichloro-4-(phenoxy)-quinoline, and 5,7-dichloro-4-(4-fluorophenoxy)quinoline, 1-oxide.

Another preferred compound for control of powdery mildew is 7-chloro-4-[(4-fluorophenyl)methyl]quinoline.

For activity against Botrytis, compounds of formula (1) wherein X and Y are CH, Z is O and $R^4$ is Cl (i.e., 8-chloro-4-quinolinyl ethers) are especially preferred. Most preferred within this class are 8-chloro-4-(2-chlorophenoxy)quinoline, 8-chloro-4-(2-chloro-4-fluorophenoxy)quinoline, and 4-(2-bromophenoxy)-8-chloroquinoline.

Although powdery mildew and Botrytis have been mentioned as being of particular interest, the data presented hereinafter will demonstrate that the compounds of the invention control many other plant pathogens as well.

Synthesis

The compounds of this invention are made using well known chemical procedures. The required starting materials are commercially available, or they are readily synthesized using standard procedures.

Synthesis of Compounds Wherein Z is O

The compounds of formula (1) wherein Z is O can be made by condensing a compound of formula (7):

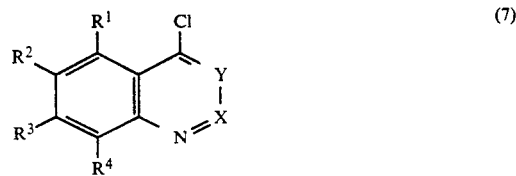

wherein $R^1$ to $R^4$ are as previously defined, with a compound of the formula (8)

HO-A    (8)

where

A is as previously defined.

The reaction can be carried out neat, at a temperature in the range of 80° to 150° C., preferably 130° to 140° C. An excess of the compound of formula (8) for example a two-fold excess, is typically used. Reaction time is typically two to 48 hours. The starting compound of formula (8) is then removed by diluting the reaction mixture with ethyl acetate, and washing with aqueous NaOH. Drying the organic layer over $MgSO_4$, and reducing pressure to remove solvent delivers the product.

In a preferred procedure, the chloride of formula (7) is reacted overnight with 1.2 to 1.4 equivalents of starting material of formula (8) in xylene at reflux.

Synthesis of Compounds Wherein Z is S

Compounds of formula (1) wherein Z is S can be prepared by reacting a compound of formula (7), as described above, with a compound of formula (9)

HS-A    (9)

where A is as previously defined, using the same procedure as for compounds wherein Z is O. Alternatively, the two reactants can be stirred in DMF with sodium hydride at 80° to 150° C.

Synthesis of Compounds Wherein Z is SO or $SO_2$

Compounds of formula (1) wherein Z is SO or $SO_2$ are prepared from compounds of formula (1) wherein Z is S using conventional oxidation procedures. For example, compounds of formula (1) wherein Z is SO can be prepared via oxidation of the sulfur atom using one equivalent of m-chloroperoxybenzoic acid in $CH_2Cl_2$ at 0° to 25° C. Similarly, compounds of formula (1)

wherein Z is SO₂ can be prepared via oxidation of the sulfur atom using 2.2 equivalents of m-chloroperoxybenzoic acid in an appropriate solvent at 0° to 25° C.

Alternatively, compounds of formula (I) wherein Z is SO₂ can be prepared by reacting a compound of formula (7), as defined above, with a sulfinate salt such as $$M^+ASO_2^- \qquad (10)$$

where M is a metal ion, such as Na⁺, Li⁺, or K⁺, and A is as described before. The reaction is generally carried out at 100° C. in a dipolar aprotic solvent, such as DMF.

Synthesis of Compounds Wherein Z is NR⁶

The compounds of formula (1) wherein Z is NR⁶ are prepared by condensing a compound of formula (7) with an amine of the formula (11)

(11)

where
R⁶′ is H or (C₁-C₄) alkyl, and
A is as previously defined.

The chloride of formula (7) is allowed to react with the amine of formula (11) at elevated temperature (100°-140° C.). One equivalent of sodium hydride is used to enhance the nucleophilic reaction. Compounds where R⁶ is (C₁-C₄) acyl are prepared from amines where R⁶=H, by reacting the amine with an acylating agent such as an acid chloride or anhydride in a basic medium for 1-3 hours at 0°-25° C.

Synthesis of Compounds Wherein Z is CR⁷R⁸

The compounds of formula (1) wherein Z is CR⁷R⁸ can be made using the process described in R. Cutler et al., *J. Am. Chem. Soc.* 71, 3375 (1949).

In this procedure, the sodium salt of the appropriate phenyl acetonitrile is allowed to react with 4,7-dichloroquinoline in benzene at reflux. The resulting diaryl substituted acetonitrile is then dissolved in n-butanol that has previously been saturated with anhydrous HCl, and the resulting mixture is refluxed for 1-18 hours. The cooled reaction mixture is concentrated in vacuo, and the residue is diluted with ethyl acetate and washed with aqueous NaOH. Drying the organic layer over MgSO₄, and reducing pressure to remove solvent delivers the desired compounds.

Derivatives

N-oxides of the compounds of formula (1) are prepared by reacting the compound of formula (1) with an oxidizing agent, such as 3-chloroperoxybenzoic acid or hydrogen peroxide, in a non-reactive organic solvent, such as methylene chloride or chloroform, at −20° C. to room temperature, preferably at about 0° C.

The acid addition salts of compounds of formula (1) are obtained in the usual way.

Thus, the invention also provides a process for preparing a compound of formula (1) which comprises
(a) condensing a compound of formula (7)

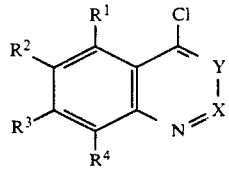
(7)

wherein R¹ to R⁴ are as defined in formula (1) with a compound of formula (8)

$$HO-A \qquad (8)$$

where A is as defined in formula (1) to provide a compound of formula (1) wherein Z is O, or (b) condensing a compound of formula (7) as defined above with a compound of the formula (9)

$$HS-A \qquad (9)$$

where A is as defined in formula (1), to provide a compound of formula (1) wherein Z is S, (c) oxidizing a compound of formula (1) wherein Z is S using a conventional procedure to provide a compound of formula (1) wherein Z is SO, or (d) oxidizing a compound of formula (1) wherein Z is S using a conventional procedure to provide a compound of formula (1) wherein Z is SO₂, or (e) condensing a compound of formula (11)

(11)

where R⁶′ is H or (C₁-C₄) alkyl and A is as defined in formula (1) to provide a compound of formula (1) wherein Z is NR⁶′, or (f) acylating a compound of formula (1) wherein Z is NR⁶′ to provide a compound of formula (1) wherein Z is NR⁶ wherein R⁶ is (C₁-C₄) acyl, or (g) reacting a compound of formula (7) as defined above with the sodium salt of a substituted acetonitrile of the formula (12)

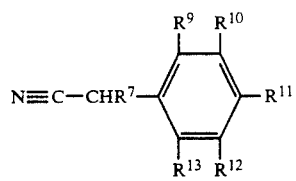
(12)

wherein R⁹ to R¹³ are as defined in formula (1) followed by acid catalyzed decynation to provide a compound of formula (1) wherein —Z—A is

(13)

(h) oxidizing a compound of formula (1) wherein Y is CH to provide the corresponding N-oxide.

Starting Materials

Phenol starting materials of formula (8) are commercially available or can be synthesized from the corresponding aniline via the Bucherer reaction, in which the aniline is reacted with aqueous sodium bisulfite. *Ang. Chem. Int. Ed. Eng.* 6, 307, 1967.

In the case of ortho-hydroxy-benzotrifluoride, a preferred preparation method is to react ortho-chlorobenzotrifluoride with sodium benzylate. The resulting ether is then hydrogenylized to provide the desired product.

Thiol starting materials of formula (9) are similarly commercially available or are synthesized using conventional procedures.

Preparation of Quinoline Starting Materials

Quinoline starting materials can be synthesized using a variety of known procedures.

*Organic Syntheses*, collective volume 3, 1955, pp. 272-75, gives a procedure for preparing 4,7-dichloroquinoline, and other polysubstituted quinolines. Another general procedure is described in *Tetrahedron*, vol. 41, pp. 3033-36 (1985).

Many of the quinoline starting materials used in the following examples were prepared as shown in the following reaction scheme

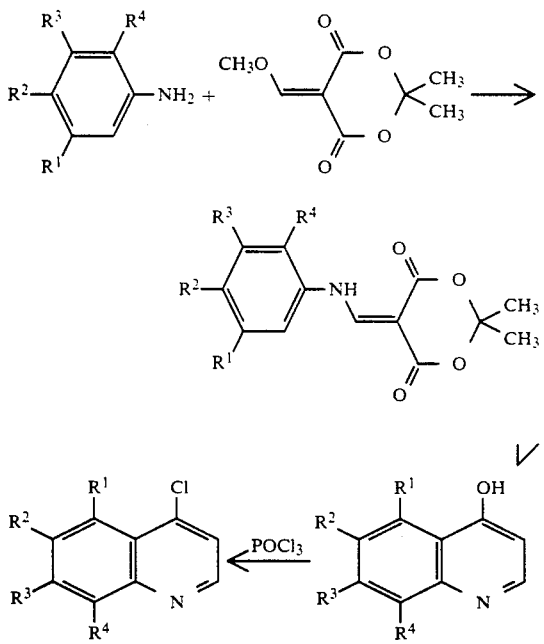

In cases where mixtures of isometric products were obtained, the mixture of substituted 4-quinolones was chlorinated under standard conditions, and the isomeric 4-chloroquinolones were separated by liquid chromatography.

4,5-dichloroquinoline was prepared by reacting 3-chloroaniline with acrylic acid in water at ambient temperature for two days. The crude product was then isolated and heated to 100° C. in solution with an excess of polyphosphoric acid, thereby furnishing a mixture of 5- and 7-chlorodihydroquinolin-4-ones. Chromatographic separation of the 5-chloro analog, followed by treatment with iodine in hot glacial acetic acid provided 4-hydroxy-5-chloroquinoline, which was halogenated to provide the desired intermediate. French Patent Number 1514280.

Other 4-chloro-5-substituted quinolines were prepared by converting the corresponding 5-substituted quinoline to the N-oxide, chlorinating, and separating the resulting mixture of 4-chloro and 2-chloro isomers using HPLC.

The 5-fluoro and 5-bromo quinolines can be prepared using the same general procedure. *J.A.C.S.*, vol. 71, 1785 (1949). The bromo-quinolines can then be lithiated and quenched with suitable electrophiles at low temperatures to provide other 5-substituted quinolines. *Chem. Ber.*, vol. 696, pp. 98 (1966).

Preparation of nitroquinolines is disclosed in *J.A.C.S.*, vol. 68, pp. 1267 (1946). Nitration of 4-chloroquinoline proceeds cleanly to deliver a mixture of 5- and 8-nitro-4-chloroquinolines, which can be separated by liquid chromatography. The 6- and 7- nitro compounds can be made via decarboxylation of the silver salts of the appropriate nitroquinoline-3-carboxylic acid.

Preparation of Cinnoline Starting Materials

Cinnoline analogs were prepared using published methods. C. M. Atkinson and J. C. Simpson - *J. Chem. Soc. London*, 1947, 232. The substituted 2-aminoacetophenone is diazotized at 0°-5° C. in water using sodium nitrite and mineral acid, and the intermediate diazonium salt is trapped by the enolic component of the ketone to provide the requisite 4-hydroxycinnoline. Routine chlorination provides the desired intermediates.

EXAMPLES

The following examples are compounds actually prepared by the above described general procedures. The melting point is given for each compound. Specific illustrative preparations for the compounds of Examples 2, 19, 21, 28, 31, 35, 114, and 116 follow the tabular listing.

TABLE 1

| | 4-(Aryloxy)quinolines | |
|---|---|---|
| EXAMPLE NUMBER | COMPOUND | M.P. |
| 1* | 7-chloro-4-[3-trifluoro-methyl)phenoxy]quinoline | 96-97° C. |
| 2* | 7-chloro-4-(4-fluorophenoxy)-quinoline | 94° C. |
| 3* | 7-chloro-4-(4-chlorophenoxy)-quinoline | 82° C. |
| 4 | 2-[(7-chloro-4-quinolinyl)-oxy]benzonitrile | 122-123° C. |
| 5* | 7-chloro-4-phenoxyquinoline | 44-46° C. |
| 6* | 7-chloro-4-(4-fluorophenoxy)-quinoline, 1-oxide | 164-165° C. |
| 7 | 7-chloro-4-(3-chlorophenoxy)-quinoline | 99-101° C. |
| 8 | 4-(2-bromophenoxy)-7-chloro-quinoline | 71-73° C. |
| 9 | 7-chloro-4-(2,4-difluoro-phenoxy)quinoline | 116-118° C. |
| 10 | 7-chloro-4-(2,3,5,6-tetra-fluorophenoxy)quinoline | 121-123° C. |
| 11 | 4-(4-fluorophenoxy)-6-methyl-quinoline | 62-63° C. |
| 12 | 7-fluoro-4-(4-fluorophenoxy)-quinoline | 76-77° C. |
| 13 | 7-chloro-4-(3-pyridinyloxy)-quinoline | 105-107° C. |
| 14 | 7-chloro-4-(2-chlorophenoxy)-quinoline | 69-70° C. |
| 15 | 7-chloro-4-(1-napthhyloxy)- | 73-76° C. |

TABLE 1-continued

4-(Aryloxy)quinolines

| EXAMPLE NUMBER | COMPOUND | M.P. |
|---|---|---|
| 16 | 7-chloro-4-(2,6-difluorophenoxy)quinoline | 134–136° C. |
| 17 | 4-(4-fluorophenoxy)-6-methoxyquinoline | 100–103° C. |
| 18 | 5,7-dichloro-4-(4-fluorophenoxy)quinoline, 1-oxide | 139–140° C. |
| 19 | 7-chloro-4-(2-chloro-4-fluorophenoxy)quinoline, 1-oxide | 177–178° C. |
| 20 | 5,7-dichloro-4-(4-fluorophenoxy)quinoline | 213–220° C. |
| 21 | 7-chloro-4-(4-fluorophenoxy)quinoline, hydrochloride | 221–224° C. |
| 22 | 8-bromo-4-(2-chlorophenoxy)quinoline | 68–71° C. |
| 23 | 7-chloro-4-[2-(i-propyl)phenoxy]quinoline | oil |
| 24 | 4-(4-fluorophenoxy)-5,7-dimethylquinoline | 92–94° C. |
| 25 | 7-chloro-4-(pentafluorophenoxy)quinoline | 95° C. |
| 26 | 4-(4-fluorophenoxy)-8-methylquinoline | oil |
| 27 | 7-chloro-4-(3-chloro-4-fluorophenoxy)quinoline | 124–127° C. |
| 28 | 5,7-dichloro-4-(4-fluorophenoxy)quinoline | 82° C. |
| 29 | 7-chloro-4-(4-phenoxyphenoxy)quinoline | 54–55° C. |
| 30 | 7-chloro-4-[4-(t-butyl)phenoxy]quinoline | 144–145° C. |
| 31 | 8-chloro-4-(2-chlorophenoxy)quinoline | 56–58° C. |
| 32 | 8-chloro-4-[2-(trifluoromethyl)phenoxy]quinoline | 64–66° C. |
| 33 | 4-(2-bromophenoxy)-8-chloroquinoline | 70–72° C. |
| 34 | 8-chloro-4-(2-flurophenoxy)quinoline | 60–62° C. |
| 35 | 8-chloro-4-(2-chloro-4-fluorophenoxy)quinoline | 99–101° C. |
| 36 | 5,7-dichloro-4-(2,4-difluorophenoxy)quinoline | 110–111° C. |
| 37 | 5,7-dichloro-4-(2-nitrophenoxy)quinoline | 84–86° C. |
| 38 | 5,7-dichloro-4-[2-(trifluoromethyl)phenoxy]quinoline | 86–89° C. |
| 39 | 5,8-dichloro-4-(2,4-difluorophenoxy)quinoline | 102–103° C. |
| 40 | 5,8-dichloro-4-(4-fluorophenoxy)quinoline | 114–115° C. |
| 41 | 6,7-dichloro-4-[2-(trifluoromethyl)phenoxy]quinoline | 146–148° C. |
| 42 | 4-(2-chloro-4-fluorophenoxy)-8-nitroquinoline | 126–128° C. |
| 43 | 8-chloro-4-(4-fluorophenoxy)-5-methylquinoline | 105–106° C. |
| 44 | 7-ethoxy-4-(4-fluorophenoxy)quinoline | 93–95° C. |
| 45 | 6-ethoxy-4-(4-fluorophenoxy)quinoline | 99–102° C. |
| 46 | 7-chloro-4-[4-(i-propyl)phenoxy]quinoline | 52–55° C. |
| 47 | 6-bromo-8-chloro-4-(4-fluorophenoxy)quinoline | 136–138° C. |
| 48 | 6-bromo-8-chloro-4-(2-chloro-4-fluorophenoxy)quinoline | 130–132° C. |
| 49 | 8-chloro-4-[4-(i-propyl)phenoxy]quinoline | 101–103° C. |
| 50 | 7-ethyl-4-(4-fluorophenoxy)quinoline | oil |
| 51 | 7-chloro-4-(3-fluorophenoxy)quinoline | 71–73° C. |
| 52 | 7-chloro-4-(2-fluorophenoxy)quinoline | 72–73° C. |
| 53 | 7-chloro-4-(4-methylphenoxy)quinoline | 78–80° C. |
| 54 | 7-chloro-4-(4-methoxyphenoxy)quinoline | 88–90° C. |
| 55 | 7-chloro-4-(2-methoxyphenoxy)quinoline | 81–83° C. |
| 56 | 7-chloro-4-(2-methylphenoxy)quinolone | 48–50° C. |
| 57 | 7-chloro-4-(3-nitrophenoxy)quinolone | 149–151° C. |
| 58 | 7-chloro-4-(2-nitrophenoxy)quinoline | 113–115° C. |
| 59 | 7-chloro-4-(4-nitrophenoxy)quinoline | 157–159° C. |
| 60 | 7-chloro-4-[2-(trifluoromethyl)phenoxy]quinoline | 59–61° C. |
| 61 | 7-chloro-4-[4-(trifluoromethyl)phenoxy]quinoline | 81–82° C. |
| 62 | 4-(2-bromo-4-fluorophenoxy)-7-chloroquinoline | 100–102° C. |
| 63 | 8-chloro-4-(2,4-dichlorophenoxy)quinoline | 165–167° C. |
| 64 | 8-chloro-4-(2-cyanophenoxy)quinoline | 119–121° C. |
| 65 | 8-chloro-4-(2,6-dichloro-4-fluorophenyl)quinoline | 161–162° C. |
| 66 | 7-nitro-4-(2-trifluoromethylphenoxy)quinoline | 110–111° C. |
| 67 | 8-chloro-4-(2-iodophenoxy)quinoline | oil |
| 68 | 7-chloro-4-(2,6-dibromo-4-fluorophenoxy) | 128–130° C. |
| 69 | 4-(4-fluorophenoxy)quinoline | 68–69° C. |
| 70 | 7-chloro-4-[3-(t-butyl)phenoxy]quinoline | oil |
| 71 | 7-chloro-4-[2-(t-butyl)phenoxy]quinoline | 90–92° C. |
| 72 | 4-[(7-chloro-4-quinolinyl)oxy]phenol | 211–213° C. |
| 73 | 2-[(7-chloro-4-quinolinyl)oxy]phenol | 209–211° C. |
| 74 | 4-([1,1'-biphenyl]-2-yloxy)-7-chloroquinoline | oil |
| 75 | 7-chloro-4-(2-chloro-4-fluorophenoxy)quinoline | 86–89° C. |
| 76 | 7-chloro-4-(2-iodophenoxy)quinoline | 68–70° C. |
| 77 | 6-chloro-4-(4-fluorophenoxy)quinoline | 98–100° C. |
| 78 | 8-fluoro-4-(4-fluorophenoxy)quinoline | 85–87° C. |
| 79 | 4-(4-fluorophenoxy)-5,7-dimethoxyquinoline | 87–89° C. |
| 80 | 4-(4-fluorophenoxy)-6-nitroquinoline | 176–178° C. |
| 81 | 4-(2-chlorophenoxy)-8-nitroquinoline | 115–117° C. |
| 82 | 4-(4-fluorophenoxy)-5-nitroquinoline | 132–134° C. |
| 83 | 7-chloro-(4-fluoro-2-nitrophenoxy)quinoline | 148–151° C. |
| 84 | 5-fluoro-4-(4-fluorophenoxy)quinoline | 91–93° C. |
| 85 | 7-bromo-4-(4-fluorophenoxy)quinoline | 87–89° C. |
| 86 | 7-chloro-6-fluoro-4-(4-fluorophenoxy)quinoline | 143–145° C. |
| 87 | 5-chloro-4-(4-fluorophenoxy)-6-methylquinoline | 110–112° C. |
| 88 | 5-chloro-6-fluoro-4-(4-fluorophenoxy)quinoline | 117–118° C. |
| 89 | 5-bromo-4-(4-fluorophenoxy)quinoline | 72–74° C. |
| 90 | 7-bromo-4-(2,4-difluorophenoxy)quinoline | 110–112° C. |
| 91 | 6-chloro-4-(4-fluorophenoxy)-8-quinolinol | 117–120° C. |
| 92 | 5,6-dichloro-4-(4-fluoro- | 114–116° C. |

TABLE 1-continued

4-(Aryloxy)quinolines

| EXAMPLE NUMBER | COMPOUND | M.P. |
|---|---|---|
| | phenoxy)quinoline | |
| 93 | 4-(4-fluorophenoxy)-6-methoxy-8-nitroquinoline | 139–141° C. |
| 94 | 5,7-dichloro-4-(2-fluorophenoxy)quinoline | 99–101° C. |
| 95 | 5,7-dichloro-4-(2-chlorophenoxy)quinoline | 78–79° C. |
| 96 | 5,7-dichloro-4-(2-cyanophenoxy)quinoline | 88–90° C. |
| 97 | 5,7-dichloro-4-(2-chloro-4-fluorophenoxy)quinoline | 83–85° C. |
| 98 | 8-chloro-4-(2,4-difluorophenoxy)quinoline | 105–107° C. |
| 99 | 7,8-dichloro-4-(2-chlorophenoxy)quinoline | 120–121° C. |
| 100 | 8-chloro-4-(3-chloro-2-nitrophenoxy)quinoline | 86–88° C. |
| 101 | 4-(2-bromo-4-fluorophenoxy)-8-chloroquinoline | 106–107° C. |
| 102 | 8-chloro-4-(3-chlorophenoxy)quinoline | 82–84° C. |
| 103 | 7-chloro-4-[4-[(trifluoromethyl)thio]phenoxy]quinoline | 90–91° C. |
| 104 | 8-chloro-4-[4-[trifluoromethyl)thio]phenoxy]quinoline | 112–114° C. |
| 105 | 4-(4-fluorophenoxy)-7-(trifluoromethoxy)quinoline | 87–88° C. |
| 106 | 4-(3-chloro-4-fluorophenxoy)-8-chloroquinoline | 88–90° C. |
| 107 | 8-chloro-4-(2-methylphenoxy)quinoline | 85–87° C. |
| 108 | 8-chloro-4-(2,6-dichlorophenoxy)quinoline | 156–159° C. |
| 109 | 8-chloro-4-(2-methoxyphenoxy)quinoline | 120–122° C. |
| 110 | 8-chloro-4-(4-methoxyphenoxy)quinoline | 119–121° C. |
| 111 | 5-chloro-4-(4-fluorophenoxy)quinoline | 62–64° C. |
| 112 | 5,7-dichloro-6-fluoro-4-(4-fluorophenoxy)quinoline | 167–169° C. |

*a compound not claimed per se

TABLE 2

4-(benzyl)quinolines

| EXAMPLE NUMBER | COMPOUND | M.P. |
|---|---|---|
| 113 | 7-chloro-4-[(4-fluorophenyl)methyl]quinoline | 100–102° C. |
| 114 | 7-chloro-α-(4-fluorophenyl)-4-quinolineacetonitrile | 118–120° C. |
| 115 | 7-chloro-4-[(4-chlorophenyl)methyl]quinoline | 98–101° C. |

TABLE 3

N-phenyl-4-quinolinamines

| EXAMPLE NUMBER | COMPOUND | M.P. |
|---|---|---|
| 116* | 7-chloro-N-(4-fluorophenyl)-4-quinolinamine | 214–216° C. |
| 117* | 7-chloro-N-(3-fluorophenyl)-4-quinolinamine | 203–208° C. |
| 118* | 7-chloro-N-(pentafluorophenyl)-4-quinolinamine | 205–207° C. |
| 119* | 7-chloro-N-(2-fluorophenyl)-4-quinolinamine | 178–179° C. |
| 120* | 7-chloro-N-(2,3,4-trifluorophenyl)-4-quinolinamine | 214–216° C. |
| 121* | 2-[(7-chloro-4-quinolinyl)amino]-6-fluorobenzonitrile | 208–210° C. |
| 122* | 8-fluoro-N-(2-fluorophenyl)-4-quinolinamine | 158–159° C. |

TABLE 3-continued

N-phenyl-4-quinolinamines

| EXAMPLE NUMBER | COMPOUND | M.P. |
|---|---|---|
| 123* | 7-chloro-N-(3,5-difluorophenyl)-4-quinolinamine monohydrate | 194–197° C. |
| 124* | 7-chloro-N-(4-fluorophenyl)-N-methyl-4-quinolinamine | 83–85° C. |
| 125* | 8-chloro-N-(2-chlorophenyl)-4-quinolinamine | 147–149° C. |

*a compound not claimed per se

TABLE 4

4-Aryloxy cinnolines

| EXAMPLE NUMBER | COMPOUND | M.P. |
|---|---|---|
| 126 | 7-chloro-4-(4-fluorophenoxy)cinnoline | 144–145° C. |

TABLE 5

Additional Compounds

| EXAMPLE NUMBER | COMPOUND | M.P. |
|---|---|---|
| 127* | 6-fluoro-2-methyl-4-[2-nitro-4-(trifluoromethyl)phenoxy]quinoline | 140° C. |
| 128* | 7-chloro-4-(4-chloro-3,5-dimethylphenoxy)quinoline | 102° C. |
| 129* | 7-chloro-4-(4-chloro-3-methylphenoxy)quinoline | 85° C. |
| 130* | 5-chloro-4-[2,6-dinitro-4-(trifluoromethyl)phenoxy]-2,8-dimethylquinoline | 189° C. |
| 131* | 8-chloro-2-methyl-4-[2-nitro-4-(trifluoromethyl)phenoxy]quinoline | 184° C. |
| 132 | 7-chloro-4-(3-methylphenoxy)quinoline | 77–79° C. |
| 133 | 4-[(7-chloro-4-quinolinyl)oxy]benzonitrile | 142–144° C. |
| 134 | 3-[(7-chloro-4-quinolinyl)oxy]benzonitrile | 133–134° C. |
| 135 | 4-(4-bromophenoxy)-7-chloroquinoline | 82–84° C. |
| 136 | 7-chloro-4-(4-iodophenoxy)quinoline | 110–113° C. |
| 137 | 4-(3-bromophenoxy)-7-chloroquinoline | 89–91° C. |
| 138* | 7-chloro-N-phenyl-4-quinolinamine | 202–204° C. |
| 139* | N-phenyl-4-quinolinamine | 205–206° C. |
| 140 | 7-chloro-4-(4-fluorophenoxy)-6-methoxyquinoline | 123–125° C. |
| 141 | 7-chloro-4-(2-methyl-3-pyrazolyloxy)quinoline | 181–183° C. |
| 142 | 8-chloro-4-(2,4-dichloro-6-fluorophenoxy)quinoline | 90–92° C. |
| 143 | 8-chloro-4-(2-ethoxyphenoxy)quinoline | 76–78° C. |
| 144 | 8-chloro-4-(4-fluoro-2-methylphenoxy)quinoline | 103–105° C. |
| 145 | 7-chloro-4-(2-methyl-4-fluorophenoxy)quinoline | 98–100° C. |
| 146 | 8-chloro-4-(4-chloro-2-fluorophenoxy)quinoline | 142–144° C. |
| 147 | 7-chloro-4-[4-[2-(4-hydroxyphenyl)ethyl]phenoxy]quinoline | 204–206° C. |
| 148 | 3-chloro-4-(4-fluorophenoxy)quinoline | 65° C. |
| 149 | 6-chloro-4-(4-fluorophenoxy)-2-methylquinoline | 188–190° C. |
| 150 | 4-(2-chlorophenoxy)-6-fluoro-2-methylquinoline | 94–96° C. |
| 151 | 4-(2,6-dibromo-4-nitrophenoxy)-8-chloroquinoline | 232–233° C. |
| 152 | 4-(4-bromo-2-fluorophenoxy)-8-chloroquinoline | 122–125° C. |
| 153 | 8-chloro-4-(2,4-dibromophenoxy)- | 115–116° C. |

TABLE 5-continued

Additional Compounds

| EXAMPLE NUMBER | COMPOUND | M.P. |
|---|---|---|
| 154 | 8-chloro-4-(4-fluoro-2-nitrophenoxy)quinoline | 133–135° C. |
| 155 | 8-chloro-4-(2,4,6-trichlorophenoxy)quinoline | 153–155° C. |
| 156 | 7-chloro-4-[(pentafluorophenyl)thio]quinoline | 130° wax |
| 157 | [4-[(7-chloro-4-quinolinyl)oxy]phenyl](4-fluorophenyl)methanone | 89–91° C. |
| 158 | 7-chloro-4-(2-pyridinyloxy)quinoline | 170–171° C. |
| 159 | 4-[1-[4-[(7-chloro-4-quinolinyl)oxy]phenyl]-2,2,2-trifluoro-1-(trifluoromethyl)ethyl]phenol | 224–226° C. |
| 160 | 7-chloro-4-[(4-fluorophenyl)thio]quinoline | 140–141° C. |
| 161 | 7-chloro-4-(4-fluorophenoxy)-2-methylquinoline | 141–142° C. |
| 162 | 8-chloro-4-(2-nitrophenoxy)quinoline | 142–144° C. |
| 163 | 4-[(4-fluorophenyl)thio]quinoline | 92–94° C. |
| 164 | 5,7-dichloro-4-(3-bromophenoxy)quinoline | 120–121° C. |
| 165 | 5,8-dichloro-4-(2-nitrophenoxy)quinoline | 120–121° C. |
| 166 | 8-bromo-4-(4-fluorophenoxy)quinoline | 122–123° C. |
| 167 | 4-(3-methoxyphenoxy)quinoline | 46–48° C. |
| 168 | 4-(3-methylphenoxy)quinoline | oil |
| 169 | 1-(4-fluorophenoxy)-8,9-dihydro-7H-cyclopenta[F]quinoline | 53–54° C. |
| 170 | 4-(4-fluorophenoxy)-7,8-dihydro-6H-cyclopenta[G]quinoline | 78–79° C. |
| 171 | 4-(4-fluorophenoxy)-7-[(trifluoromethyl)thio]quinoline | 78–80° C. |
| 172* | 4-phenoxy-6-nitroquinoline | N/A |
| 173 | 5,7-dichloro-4-(4-fluorophenoxy)-6-methylquinoline | 110–112° C. |
| 174 | 4-(4-fluorophenoxy)-7-(methylthio)quinoline | 87–89° C. |
| 175 | 7-chloro-4-(2,4-dinitrophenoxy)quinoline | 181–183° C. |
| 176 | 4-(4-fluorophenoxy)-6-fluoro-2-methylquinoline | 126–128° C. |
| 177 | 8-chloro-4-(2,6-dibromo-4-fluorophenoxy)quinoline | 195–197° C. |
| 178 | 5-chloro-2,8-dimethyl-4-(4-fluorophenoxy)quinoline | 75–76° C. |
| 179 | 8-chloro-4-(3-methylphenoxy)quinoline | 46–48° C. |
| 180 | 4-(4-fluorophenoxy)-5-methoxy-7-trifluoromethylquinoline | 108–110° C. |
| 181* | 4-(2-bromophenylamino)-8-chloroquinoline | 147–149° C. |
| 182 | 7-chloro-4-[2-(methylthio)phenoxy]quinoline | 107–108° C. |
| 183 | 7-chloro-4-(4-ethoxyphenoxy)quinoline | 113–115° C. |
| 184 | 8-chloro-4-(4-ethoxyphenoxy)quinoline | 94–96° C. |
| 185 | 5,7-dichloro-4-phenoxyquinoline | 97–99° C. |
| 186 | 8-chloro-4-[(2-chlorophenyl)thio]quinoline | 112–114° C. |
| 187 | 7-chloro-4-(3-methoxyphenoxy)quinoline | 69–70° C. |
| 188 | 8-chloro-4-(4-iodophenoxy)quinoline | 114–116° C. |
| 189 | 4-(4-fluorophenoxy)-7-nitroquinoline | 159–161° C. |
| 190 | 8-chloro-4-(4-chloro-2-methylphenoxy)quinoline | 143–145° C. |
| 191 | 4-(4-chloro-3,5-dimethylphenoxy)-8-chloroquinoline | 128–129° C. |
| 192 | 4-(4-chloro-2-nitrophenoxy)-8-chloroquinoline | 149–150° C. |
| 193 | 7-chloro-4-(3-pyridazinyloxy)quinoline | 158–160° C. |
| 194 | 8-chloro-4-(2-ethylphenoxy)quinoline | oil |
| 195 | 7-chloro-4-[(4-chloro-1-naphthalenyl)oxy]quinoline | 120–122° C. |
| 196 | 8-chloro-4-(4-fluorophenoxy)cinnoline | 160–163° C. |
| 197 | 4-[(1,1'-biphenyl)-4-yloxy]-7-chloroquinoline | 139–141° C. |
| 198 | 3-[(7-chloro-4-quinolinyl)oxy]phenol | 150–154° C. |
| 199 | 7-chloro-4-(2-phenoxyphenoxy)quinoline | 84–86° C. |
| 200 | 4-(4-fluorophenoxy)-8-(trifluoromethyl)quinoline | 101–102° C. |
| 201 | 6,8-difluoro-4-(4-fluorophenoxy)quinoline | 118–119° C. |
| 202 | 7-chloro-4-(1,3-benzodioxol-5-yloxy)quinoline | 85–87° C. |
| 203 | 4-(1,3-benzodioxol-5-yloxy)-8-chloroquinoline | 120–122° C. |
| 204 | 8-chloro-4-[2-(methylthio)phenoxy]quinoline | 67–69° C. |
| 205 | 8-chloro-4-(4-methylphenoxy)quinoline | 97–98° C. |
| 206* | 8-chloro-N-(2-chloro-4-fluorophenyl)-4-quinolinamine | 163–165° C. |
| 207 | 8-chloro-4-(2,3-dimethylphenoxy)quinoline | 118–120° C. |
| 208 | 8-chloro-4-(3,4-dimethylphenoxy)quinoline | .88–90° C. |
| 209 | 7-chloro-4-[4-(trifluoromethoxy)phenoxy]quinoline | 79–80° C. |
| 210 | 8-chloro-4-[4-(trifluoromethoxy)phenoxy]quinoline | 131–133° C. |
| 211 | 8-chloro-4-(2,5-dichlorophenoxy)quinoline | 70–73° C. |
| 212 | 8-chloro-4-(2,6-dimethylphenoxy)quinoline | 125–127° C. |
| 213 | 8-chloro-4-(3,5-dimethylphenoxy)quinoline | 85–87° C. |
| 214 | 8-chloro-4-(2-chloro-6-methylphenoxy)quinoline | 154–156° C. |
| 215 | 8-chloro-4-(2,5-dimethylphenoxy)quinoline | 51–53° C. |
| 216 | 8-chloro-4-[2-chloro-5-((trifluoromethyl)phenoxy]quinoline | 120–122° C. |
| 217 | 4-(2-chloro-4-nitrophenoxy)-8-chloroquinoline | 179–181° C. |
| 218 | 8-chloro-α-(2-chlorophenyl)-4-quinolineacetonitrile | 135–137° C. |
| 219 | 6,8-dichloro-4-(4-fluorophenoxy)quinoline | 136–138° C. |
| 220* | 4-phenoxyquinoline | oil |
| 221 | 6,8-dichloro-4-(2-chlorophenoxy)quinoline | 98–100° C. |
| 222 | 4-(4-fluorophenoxy)-8-nitroquinoline | 128–130° C. |
| 223 | 4-(2-cyanophenoxy)-5,6,7-trichloroquinoline | 163–165° C. |
| 224 | 5,6,7-trichloro-4-(2-chloro-4-fluorophenoxy)quinoline | 182–184° C. |
| 225 | 4-(2,4-dibromophenoxy)-7-chloroquinoline | 134–136° C. |
| 226 | 5,6,7-trichloro-4-(4-fluorophenoxy)quinoline | 161–163° C. |
| 227 | 4-(4-bromo-2-fluorophenoxy)-7-chloroquinoline | 129–131° C. |
| 228 | 7-chloro-4-[tricyclo(3.3.1.1-(3,7))-Dec-2-yloxy]quinoline | 136–138° C. |
| 229 | 8-chloro-4-[[1-(3-chlorophenyl)-1H-tetrazol-5-yl]oxy]quinoline | 148–150° C. |
| 230 | 8-chloro-4-(4-ethylphenoxy)quinoline | 70–72° C. |
| 231 | 7-chloro-4-(2,6-dimethylphenoxy)quinoline | 54–56° C. |
| 232 | 7-chloro-4-pyrazol(oxy)quinoline | 190–192° C. |
| 233 | 8-fluoro-4-(2-phenylphenoxy)quinoline | N/A |
| 234 | 4-(2-chloro-4,6-difluoro- | 99–101° C. |

TABLE 5-continued

Additional Compounds

| EXAMPLE NUMBER | COMPOUND | M.P. |
|---|---|---|
| | phenoxy)-8-chloroquinoline | |
| 235 | 7-chloro-4-(4-fluorophenoxy)-6-methylquinoline | 121–123° C. |
| 236 | 6,7-dichloro-4-(4-fluorophenoxy)-quinoline | 134–136° C. |
| 237 | 7,8-dichloro-4-(4-fluorophenoxy)-quinoline | 144–145° C. |
| 238 | 2-[(7,8-dichloro-4-quinolinyl)oxy]-benzonitrile | 153–154° C. |
| 239 | 2-chloro-4-(4-fluorophenoxy)-quinoline | 142–144° C. |
| 240 | 7,8-dichloro-4-(2,4-difluoro-phenoxy)quinoline | 153–154° C. |
| 241 | 7,8-dichloro-4-(2-fluorophenoxy)-quinoline | 143–145° C. |
| 242* | 2-methyl-4-phenoxyquinoline | 71–72° C. |
| 243 | 8-chloro-4-[(1-methylcyclopentyl)-oxy]quinoline | 82–83° C. |
| 244 | 5,6,7,8-tetrachloro-4-(4-fluoro-phenoxyquinoline | N/A |
| 245 | 4-[(5,7-dichloro-4-quinolinyl)-oxy]benzonitrile | 161–163° C. |
| 246 | 7-chloro-4-(methylthio)quinoline | 102–104° C. |
| 247 | 3-bromo-7-chloro-4-(2,4-difluoro-phenoxy)quinoline | 113–114° C. |
| 248 | 3-bromo-7-chloro-4-(4-fluoro-phenoxy)quinoline | 96.5–98° C. |
| 249 | 3-bromo-4-(2-chloro-4-fluoro-phenoxy)-7-chloroquinoline | 140–141° C. |
| 250 | 3-bromo-4-(2-chlorophenoxy)-7-chloroquinoline | 146–148° C. |
| 251 | 3-bromo-4-(2-bromo-4-fluoro-phenoxy)-7-chloroquinoline | 152–154° C. |
| 252 | 7-chloro-4-(methylsulfonyl)-quinoline | 164–166° C. |
| 253 | 8-chloro-4-(methylsulfonyl)-quinoline | 98–100° C. |
| 254 | 3-bromo-7-chloro-4-(methyl-sulfonyl)quinoline | 140–142° C. |

*a compound not claimed per se

The following detailed descriptions of the procedures used to prepare selected examples are representative of the procedure used to prepare the compounds of the other examples.

EXAMPLES 2 and 21

7-Chloro-4-(4-fluorophenoxy)quinoline and 7-Chloro-4-(4-fluorophenoxy)quinoline, hydrochloride

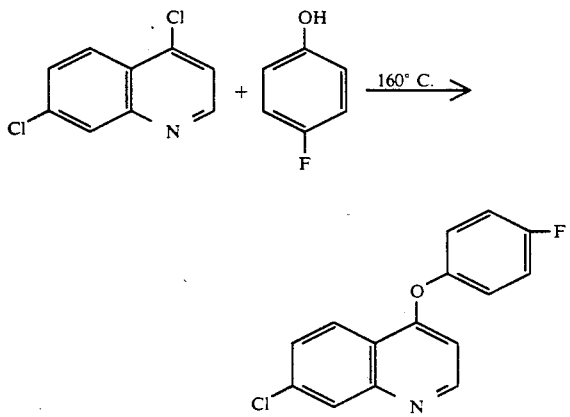

A slurry comprising 7.92 g (0.04 mol) of 4,7-dichloroquinoline, 4.48 g (0.04 mol) of 4-fluorophenol, and 24 ml of xylene was stirred and heated to reflux. The resulting clear orange solution was refluxed at 144° C. for 17 hours, at which time an additional 0.90 g (0.008 mol) of 4-fluorophenol was added, and refluxing was continued. The mixture was concentrated to a brown resin, which was dissolved in a mixture of $CH_2Cl_2$ (50 ml) and 1N NaOH (50 ml). The organic layer was washed four times with 50 ml of 1N NaOH, then dried with $Na_2SO_4$, and concentrated to a brown oil (9.8 g), which crystallized. The product, 7-chloro-4-(4-fluorophenoxyl)quinoline, was recrystallized from hexane, yielding a white crystalline solid. Yield: 8.01 g (73.2%). M.P. 91°–92° C.

The corresponding amine hydrochloride, was prepared using a similar procedure, except that after refluxing the reaction mixture of 18 hours, the mixture was cooled to room temperature, and anhydrous HCl was added over one half hour period. The mixture was then cooled to 0° C. and held at 0° C. for two hours. The mixture was then filtered and the product dried under vacuum at 40° C. The filtrate was stirred 48 hours at room temperature, during which time additional product precipitated. The product, 7-chloro-4-(4-fluorophenoxy)quinoline, hydrochloride, was recrystallized from 40 ml propanol. Yield: 9.10 g (73%). M.P. 220°–224° C.

Example 19

7-Chloro-4-(2-chloro-4-fluorophenoxy)quinoline 1-oxide

A mixture of 5.0 g (16.22 mmol) of 4-(2-chloro-4-fluorophenoxy)-7-chloroquinoline, 4.20 g (19.47 mmol) of 80% 3-chloroperoxybenzoic acid, and 50 ml of $CH_2Cl_2$ was stirred at 0° C. for six hours. The $CH_2Cl_2$ was removed by reducing pressure, and the residue was dissolved in ethyl acetate and washed with base. After removing solvent from the organic layer by reducing pressure, a white solid formed. This was recrystallized in ethyl acetate. Yield 3.04 g (58%). M.P. 177°–178° C.

Analysis: Theory: C, 55.58; H, 2.49; N, 4.32; Found: C, 55.67; H, 2.46; N, 4.43.

Example 28

5,7-Dichloro-4-(4-fluorophenoxy)quinoline

A mixture of 29.11 g of 4,5,7-trichloroquinoline and 16.84 g of 4-fluorophenol was heated to 160° C. After approximately 40 minutes, the molten solution solidified. The solid was dissolved in ethyl acetate and 2N NaOH. The organic layer was washed with base to remove excess phenol, then dried. Solvent was removed by reducing pressure, and the residue was purified by recrystallizing in heptane to produce 29.49 g of the title product. M.P. 105°–106° C.

Analysis Theory: C, 58.47; H, 2.62; N, 4.55; Found: C, 58.38; H, 2.52; N, 4.55.

Example 31

8-chloro-4-(2-chlorophenoxy)quinoline

A mixture of 2.0 g of 4,8-dichloroquinoline and 2.6 g of 2-chlorophenol was heated to 160° C. and stirred. Progress of the reaction was monitored by TLC. When no 4,8-dichloroquinoline remained, the reaction mixture was diluted with ethyl acetate, and washed with base to remove most of the excess phenol. To remove phenol remaining after washing, the product was purified using HPLC. Fractions containing product were combined, and solvent was removed using reduced pressure. The oily product crystallized. Yield: 1.36 g (46%). M.P. 56°-58° C.

Analysis Theory: C, 62.09; H, 3.13; N, 4.83; Found: C, 62.14; H, 3.11; N, 5.04.

Example 35

8-chloro-4-(2-chloro-4-fluorophenoxy)quinoline

A mixture of 2.0 g of 4,8-dichloroquinoline and 2.96 g of 2-chloro-4-fluorophenol was heated to 160° C. and stirred. Progress of the reaction was monitored using TLC. When no 4,8-dichloroquinoline remained, the product was washed with base to remove phenol, then purified using HPLC. A brown solid resulted, which was recrystallized in heptane to give 1.54 g of the title product as yellow crystals. Yield: 49%. M.P. 99°-101° C.

Analysis: Theory: C, 58.47; H, 2.62; N, 4.55; Found: C, 58.39; H, 2.85; N, 4.49.

Example 114

7-chloro-4-[(4-fluorophenyl)methyl]quinoline

A solution of 100 g (740 mmol) of 4-fluorophenylacetonitrile in 200 ml of benzene was added to a cooled (0° C.) slurry of 40 g (945 mmol) of sodium amide in 600 ml of the same solvent. After the addition was complete the solution was warmed to ambient temperature and stirred for one-half hour. The reaction mixture was again cooled to 0° C., 73.2 g (370 mmol) of solid 4,7-dichloroquinoline was added in increments, and the mixture was then stirred at ambient temperature overnight. Quenching with NH$_4$Cl followed by workup gave the crude disubstituted acetonitrile, which was dissolved in 500 ml of n-butanol saturated with anhydrous HCl. The acidic solution was heated at reflux for 18 hours. The majority of the solvent was removed via distillation, and the residue was diluted with solvent, and washed with 10% NaOH. The organic layer was dried, and the solvent was removed in vacuo. Purification via HPLC gave 67 g of the title product. Yield: 67%.

Example 116

7-chloro-N-(4-fluorophenyl)-4-quinolinamine

To 2.0 g of 4,7-dichloroquinoline was added 2.24 g of 4-fluoroaniline, and the mixture was heated with stirring to 160° C. After a few minutes at this temperature, the mixture smoked and the melt solidified. The solid was allowed to cool and was then dissolved in ethyl acetate and washed to remove the aniline. The organic layer was dried over MgSO$_4$ and then solvent was removed using reduced pressure. The residue was recrystallized in heptane to yield 1.27 g of 7-chloro-N-(4-fluorophenyl)-4-quinolinamine. M.P. 214°-16° C. (46.1% yield).

Analysis: Theory: C, 66.07; H, 3.70; N, 10.27; Found: C, 66.34; H, 3.83; N, 10.56.

Utility

The compounds of formula (1) have been found to control fungi, particularly plant pathogens. When employed in the treatment or prevention of plant fungal diseases, the compounds are applied to seeds or plants in a disease inhibiting and phytologically acceptable amount. The term "disease inhibiting and phytologically acceptable amount," as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. The compounds of the invention may also be used to protect stored grain and other non-plant loci from fungal infestation.

Greenhouse Tests

The following experiments were performed in the laboratory to determine the fungicidal efficacy of the compounds of the invention.

Test 1

This screen was used to evaluate the efficacy of the present compounds against a variety of different organisms that cause plant diseases.

The test compounds were formulated for application by dissolving 50 mg of the compound in 1.25 ml of solvent. The solvent was prepared by mixing 50 ml of "Tween 20" (polyoxyethylene (20) sorbitan monolaurate surfactant) with 475 ml of acetone and 475 ml of ethanol. The solvent/compound solution was diluted to 125 ml with deionized water. The resulting formulation contains 400 ppm test chemical. Lower concentrations were obtained by serial dilution with the solvent-surfactant mixture.

The formulated test compounds were applied by foliar spray. The following plant pathogens and their corresponding plants were employed.

| Pathogen | Designation in Following Tables | Host |
|---|---|---|
| *Erysiphe graminis tritici* (powdery mildew) | POWD MDEW | wheat |
| *Pyricularia oryzae* (rice blast) | RICE BLAS | rice |
| *Puccinia recondita tritici* (leaf rust) | LEAF RUST | wheat |
| *Botrytis cinerea* (gray mold) | GRAY MOLD | grape berries |
| *Pseudoperonospora cubensis* (downy mildew) | DOWN MDEW | squash |
| *Cercospora beticola* (leaf spot) | LEAF SPOT | sugar beet |
| *Venturia inaequalis* (apple scab) | APPL SCAB | apple seedling |
| *Septoria tritici* (leaf blotch) | LEAF BLOT | wheat |

The formulated technical compounds were sprayed on all foliar surfaces of the host plants (or cut berry) to past run-off. Single pots of each host plant were placed on raised, revolving pedestals in a fume hood. Test solutions were sprayed on all foliar surfaces. All treatments were allowed to dry and the plants were inoculated with the appropriate pathogens within 2-4 hours.

The effectiveness of test compounds in controlling disease was rated using the following scale:

0 = not tested against specific organism
− = 0-19% control at 400 ppm
+ = 20-89% control at 400 ppm
+ + = 90-100% control at 400 ppm
+ + + = 90-100% control at 100 ppm Results are reported in the following Table 6:

TABLE 6

| COMPOUND EX NO. | POWD MDEW | RICE BLAS | LEAF RUST | GRAY MOLD | DOWN MDEW | LEAF SPOT | APPL SCAB | LEAF BLOT |
|---|---|---|---|---|---|---|---|---|
| 1 | + | − | − | − | − | − | − | + |
| 2 | +++ | − | − | − | + | 0 | − | + |
| 3 | ++ | − | − | − | + | 0 | − | + |
| 4 | +++ | − | − | − | − | − | − | − |
| 5 | ++ | + | + | − | − | + | − | − |
| 6 | +++ | − | + | − | + | ++ | − | + |
| 7 | ++ | − | − | − | − | − | − | − |
| 8 | +++ | − | − | − | + | − | − | + |
| 9 | +++ | − | − | − | − | + | − | + |
| 10 | + | − | + | − | + | + | − | + |
| 11 | + | + | ++ | − | ++ | − | + | + |
| 12 | + | − | + | − | ++ | − | − | − |
| 13 | + | − | ++ | − | + | − | + | − |
| 14 | +++ | − | + | − | − | − | − | − |
| 15 | ++ | + | − | − | ++ | + | − | − |
| 16 | ++ | − | − | − | + | − | − | − |
| 17 | +++ | + | ++ | − | + | − | − | − |
| 18 | +++ | + | − | − | − | + | − | − |
| 19 | ++ | − | − | − | ++ | + | − | + |
| 20 | +++ | − | − | − | + | 0 | 0 | 0 |
| 21 | +++ | − | − | − | − | 0 | 0 | 0 |
| 22 | +++ | ++ | − | ++ | ++ | 0 | 0 | 0 |
| 23 | ++ | ++ | − | + | + | 0 | 0 | 0 |
| 24 | +++ | ++ | ++ | − | − | 0 | 0 | 0 |
| 25 | + | − | − | − | − | − | − | − |
| 26 | + | − | + | − | + | − | − | − |
| 27 | + | − | − | − | − | 0 | 0 | 0 |
| 28 | +++ | − | + | − | − | + | − | − |
| 29 | +++ | + | − | − | + | − | − | − |
| 30 | + | − | + | − | − | 0 | 0 | − |
| 31 | + | ++ | + | +++ | ++ | + | +++ | − |
| 32 | + | + | − | − | − | − | − | + |
| 33 | + | + | − | +++ | + | − | + | − |
| 34 | + | − | − | + | − | 0 | 0 | 0 |
| 35 | + | − | + | +++ | + | − | +++ | + |
| 36 | +++ | − | − | − | − | 0 | 0 | 0 |
| 37 | + | + | − | − | ++ | 0 | 0 | 0 |
| 38 | ++ | + | − | − | − | 0 | 0 | 0 |
| 39 | +++ | + | − | − | − | − | − | − |
| 40 | ++ | + | − | − | − | − | − | − |
| 41 | ++ | − | − | − | − | 0 | 0 | 0 |
| 42 | − | − | − | + | − | 0 | 0 | 0 |
| 43 | ++ | − | − | − | − | 0 | 0 | 0 |
| 44 | + | + | + | − | − | 0 | 0 | 0 |
| 45 | + | − | − | − | + | 0 | 0 | 0 |
| 46 | + | − | − | − | − | 0 | 0 | 0 |
| 47 | − | − | − | − | + | 0 | 0 | 0 |
| 48 | ++ | − | − | − | − | 0 | 0 | 0 |
| 49 | − | − | − | + | − | 0 | 0 | 0 |
| 50 | ++ | − | ++ | − | ++ | 0 | 0 | 0 |
| 51 | ++ | + | − | − | − | − | − | + |
| 52 | +++ | − | − | − | − | + | − | + |
| 53 | − | − | − | − | − | 0 | 0 | 0 |
| 54 | ++ | − | + | − | + | − | − | − |
| 55 | + | − | + | − | ++ | − | + | − |
| 56 | + | + | + | − | + | − | − | − |
| 57 | + | − | − | − | − | − | − | − |
| 58 | ++ | − | − | − | − | − | − | + |
| 59 | ++ | + | − | − | − | − | − | − |
| 60 | +++ | + | − | − | + | − | − | − |
| 61 | + | − | − | − | + | 0 | 0 | 0 |
| 62 | +++ | + | + | − | − | 0 | 0 | 0 |
| 63 | + | − | − | − | − | 0 | 0 | 0 |
| 64 | + | + | − | − | + | 0 | 0 | 0 |
| 65 | + | − | − | + | + | 0 | 0 | 0 |
| 66 | ++ | − | − | − | − | 0 | 0 | 0 |
| 67 | ++ | ++ | + | ++ | + | 0 | 0 | 0 |
| 68 | + | − | − | − | − | 0 | 0 | 0 |
| 69 | + | − | ++ | − | ++ | − | − | − |
| 70 | ++ | + | + | − | + | − | − | + |
| 71 | ++ | + | − | − | − | − | − | + |
| 72 | − | − | + | − | + | 0 | 0 | 0 |
| 73 | − | − | − | − | − | 0 | 0 | 0 |
| 74 | + | + | − | − | + | − | − | + |
| 75 | ++ | − | − | − | − | − | − | + |
| 76 | +++ | − | + | − | − | − | − | + |
| 77 | − | − | + | − | − | 0 | 0 | 0 |
| 78 | − | + | + | + | ++ | − | + | + |
| 79 | − | ++ | + | − | + | 0 | 0 | 0 |

TABLE 6-continued

| COMPOUND EX NO. | POWD MDEW | RICE BLAS | LEAF RUST | GRAY MOLD | DOWN MDEW | LEAF SPOT | APPL SCAB | LEAF BLOT |
|---|---|---|---|---|---|---|---|---|
| 80 | + | − | − | − | − | 0 | 0 | 0 |
| 81 | − | + | − | + | − | 0 | 0 | 0 |
| 82 | +++ | − | + | − | − | 0 | 0 | 0 |
| 83 | ++ | − | − | − | − | 0 | 0 | 0 |
| 84 | + | + | ++ | − | ++ | 0 | 0 | 0 |
| 85 | +++ | + | + | − | − | 0 | 0 | 0 |
| 86 | +++ | − | − | − | − | 0 | 0 | 0 |
| 87 | − | − | + | − | − | 0 | 0 | 0 |
| 88 | ++ | − | +++ | − | − | 0 | 0 | 0 |
| 89 | +++ | + | +++ | − | − | 0 | 0 | 0 |
| 90 | +++ | − | − | − | − | 0 | 0 | 0 |
| 91 | ++ | +++ | +++ | + | +++ | 0 | 0 | 0 |
| 92 | − | − | ++ | − | − | 0 | 0 | 0 |
| 93 | ++ | − | − | − | − | 0 | 0 | 0 |
| 94 | + | − | − | − | − | 0 | 0 | 0 |
| 95 | +++ | − | − | − | − | − | − | + |
| 96 | + | ++ | − | − | + | − | − | + |
| 97 | +++ | − | − | − | + | − | − | − |
| 98 | + | + | − | ++ | ++ | 0 | 0 | 0 |
| 99 | − | − | − | + | − | 0 | 0 | 0 |
| 100 | − | ++ | + | ++ | + | 0 | 0 | 0 |
| 101 | + | + | − | ++ | + | 0 | 0 | 0 |
| 102 | + | − | + | + | − | 0 | 0 | 0 |
| 103 | ++ | − | − | − | − | 0 | 0 | 0 |
| 104 | + | − | − | + | − | 0 | 0 | 0 |
| 105 | + | − | − | − | − | 0 | 0 | 0 |
| 106 | − | − | + | ++ | + | 0 | 0 | 0 |
| 107 | ++ | ++ | + | ++ | ++ | 0 | 0 | 0 |
| 108 | ++ | − | − | + | − | 0 | 0 | 0 |
| 109 | + | + | − | + | − | 0 | 0 | 0 |
| 110 | − | − | − | ++ | − | 0 | 0 | 0 |
| 111 | ++ | + | ++ | − | − | 0 | 0 | 0 |
| 112 | +++ | − | − | − | − | 0 | 0 | 0 |
| 113 | +++ | − | − | − | − | − | − | ++ |
| 114 | ++ | − | − | − | + | + | − | − |
| 115 | ++ | − | − | − | − | 0 | 0 | 0 |
| 116 | − | − | − | + | − | + | 0 | 0 |
| 117 | − | − | − | − | + | 0 | 0 | 0 |
| 118 | − | − | + | − | +++ | ++ | − | + |
| 119 | + | + | − | − | ++ | + | − | − |
| 120 | − | − | + | − | − | 0 | 0 | 0 |
| 121 | + | − | + | − | − | 0 | 0 | 0 |
| 122 | − | + | − | − | ++ | − | − | − |
| 123 | + | − | − | − | − | 0 | 0 | 0 |
| 124 | ++ | + | + | − | + | + | − | + |
| 125 | − | + | − | − | + | 0 | 0 | 0 |
| 126 | +++ | − | + | − | − | + | − | − |
| 127 | − | − | − | − | − | 0 | 0 | 0 |
| 128 | + | − | − | − | − | 0 | 0 | 0 |
| 129 | ++ | − | − | − | − | − | − | − |
| 130 | − | − | + | − | − | − | − | − |
| 131 | − | − | + | − | − | 0 | 0 | 0 |
| 132 | ++ | − | + | − | − | − | − | − |
| 133 | − | − | − | − | − | 0 | 0 | 0 |
| 134 | + | − | − | − | + | 0 | 0 | 0 |
| 135 | + | − | − | − | − | 0 | 0 | 0 |
| 136 | − | − | − | − | − | 0 | 0 | 0 |
| 137 | − | − | + | − | − | 0 | 0 | 0 |
| 138 | − | − | + | − | ++ | + | − | − |
| 139 | − | − | − | − | + | 0 | 0 | 0 |
| 140 | − | 0 | − | − | − | 0 | 0 | 0 |
| 141 | + | − | + | − | + | 0 | 0 | 0 |
| 142 | ++ | + | − | ++ | + | 0 | 0 | 0 |
| 143 | + | + | − | − | + | 0 | 0 | 0 |
| 144 | ++ | − | − | ++ | − | 0 | 0 | 0 |
| 145 | +++ | − | − | − | − | 0 | 0 | 0 |
| 146 | − | − | − | ++ | − | 0 | 0 | 0 |
| 147 | − | − | − | − | − | 0 | 0 | 0 |
| 148 | − | + | − | − | + | 0 | 0 | 0 |
| 149 | − | + | − | − | − | 0 | 0 | 0 |
| 150 | ++ | + | + | − | + | 0 | 0 | 0 |
| 151 | − | − | − | − | − | 0 | 0 | 0 |
| 152 | + | + | − | ++ | + | 0 | 0 | 0 |
| 153 | − | − | − | + | − | 0 | 0 | 0 |
| 154 | − | + | − | + | + | 0 | 0 | 0 |
| 155 | − | − | − | − | − | 0 | 0 | 0 |
| 156 | + | − | − | − | + | 0 | 0 | 0 |
| 157 | + | − | − | − | − | 0 | 0 | 0 |
| 158 | + | − | − | − | − | 0 | 0 | 0 |

TABLE 6-continued

| COMPOUND EX NO. | POWD MDEW | RICE BLAS | LEAF RUST | GRAY MOLD | DOWN MDEW | LEAF SPOT | APPL SCAB | LEAF BLOT |
|---|---|---|---|---|---|---|---|---|
| 159 | − | − | + | − | − | 0 | 0 | 0 |
| 160 | + | − | − | − | − | 0 | 0 | 0 |
| 161 | + | − | − | − | − | 0 | 0 | 0 |
| 162 | − | − | − | − | − | 0 | 0 | 0 |
| 163 | + | − | + | − | − | 0 | 0 | 0 |
| 164 | + | − | − | − | − | 0 | 0 | 0 |
| 165 | + | − | − | − | − | 0 | 0 | 0 |
| 166 | − | − | − | − | − | 0 | 0 | 0 |
| 167 | ++ | + | ++ | − | + | 0 | 0 | 0 |
| 168 | + | + | + | − | + | 0 | 0 | 0 |
| 169 | ++ | + | ++ | − | ++ | 0 | 0 | 0 |
| 170 | + | + | ++ | − | + | 0 | 0 | 0 |
| 171 | − | − | − | − | − | 0 | 0 | 0 |
| 172 | − | − | − | − | − | 0 | 0 | 0 |
| 173 | − | − | − | − | − | 0 | 0 | 0 |
| 174 | − | − | − | − | ++ | 0 | 0 | 0 |
| 175 | + | − | − | − | − | 0 | 0 | 0 |
| 176 | − | + | − | − | − | 0 | 0 | 0 |
| 177 | − | − | − | − | − | 0 | 0 | 0 |
| 178 | − | − | − | − | + | 0 | 0 | 0 |
| 179 | ++ | − | − | ++ | − | 0 | 0 | 0 |
| 180 | ++ | + | − | − | + | 0 | 0 | 0 |
| 181 | − | + | − | − | ++ | 0 | 0 | 0 |
| 182 | + | − | − | − | − | 0 | 0 | 0 |
| 183 | + | + | + | − | − | 0 | 0 | 0 |
| 184 | − | − | − | − | − | 0 | 0 | 0 |
| 185 | +++ | − | + | − | − | 0 | 0 | 0 |
| 186 | + | − | − | − | − | 0 | 0 | 0 |
| 187 | + | − | + | − | + | 0 | 0 | 0 |
| 188 | − | − | − | − | − | 0 | 0 | 0 |
| 189 | − | − | − | − | − | 0 | 0 | 0 |
| 190 | − | − | − | ++ | − | 0 | 0 | 0 |
| 191 | − | − | − | − | − | 0 | 0 | 0 |
| 192 | + | + | + | − | + | 0 | 0 | 0 |
| 193 | − | + | + | − | − | 0 | 0 | 0 |
| 194 | +++ | + | − | ++ | ++ | 0 | 0 | 0 |
| 195 | − | − | − | − | + | 0 | 0 | 0 |
| 196 | − | − | − | − | − | 0 | 0 | 0 |
| 197 | + | − | − | − | − | 0 | 0 | 0 |
| 198 | − | − | − | − | − | 0 | 0 | 0 |
| 199 | + | − | − | − | − | 0 | 0 | 0 |
| 200 | − | − | − | − | − | 0 | 0 | 0 |
| 201 | − | − | − | − | − | 0 | 0 | 0 |
| 202 | ++ | − | + | − | − | 0 | 0 | 0 |
| 203 | − | − | + | − | − | 0 | 0 | 0 |
| 204 | − | − | − | + | − | 0 | 0 | 0 |
| 205 | + | + | − | + | − | 0 | 0 | 0 |
| 206 | − | − | − | − | ++ | 0 | 0 | 0 |
| 207 | + | + | − | ++ | − | 0 | 0 | 0 |
| 208 | − | − | − | + | − | 0 | 0 | 0 |
| 209 | +− | − | − | − | − | 0 | 0 | 0 |
| 210 | − | − | − | − | − | 0 | 0 | 0 |
| 211 | − | + | − | ++ | ++ | 0 | 0 | 0 |
| 212 | ++ | − | − | − | + | 0 | 0 | 0 |
| 213 | − | − | − | + | − | 0 | 0 | 0 |
| 214 | + | − | − | + | − | 0 | 0 | 0 |
| 215 | ++ | + | + | + | ++ | 0 | 0 | 0 |
| 216 | − | − | − | − | + | 0 | 0 | 0 |
| 217 | − | − | − | − | − | 0 | 0 | 0 |
| 218 | − | − | − | − | − | 0 | 0 | 0 |
| 219 | + | − | − | − | − | 0 | 0 | 0 |
| 220 | + | + | + | − | ++ | 0 | 0 | 0 |
| 221 | − | + | − | − | − | 0 | 0 | 0 |
| 222 | − | − | − | − | − | 0 | 0 | 0 |
| 223 | − | − | − | − | − | 0 | 0 | 0 |
| 224 | + | − | − | − | − | 0 | 0 | 0 |
| 225 | + | − | − | − | − | 0 | 0 | 0 |
| 226 | − | − | − | − | − | 0 | 0 | 0 |
| 227 | + | − | − | − | − | 0 | 0 | 0 |
| 228 | + | − | − | − | − | 0 | 0 | 0 |
| 229 | + | − | − | − | − | 0 | 0 | 0 |
| 230 | ++ | + | + | + | − | 0 | 0 | 0 |
| 231 | ++ | ++ | + | − | + | 0 | 0 | 0 |
| 232 | + | − | − | − | + | 0 | 0 | 0 |
| 233 | ++ | − | + | + | ++ | 0 | 0 | 0 |
| 234 | +++ | ++ | − | +++ | − | 0 | 0 | 0 |
| 235 | + | − | − | − | − | 0 | 0 | 0 |
| 236 | − | − | − | − | − | 0 | 0 | 0 |
| 237 | − | − | − | − | − | 0 | 0 | 0 |

TABLE 6-continued

| COMPOUND EX NO. | POWD MDEW | RICE BLAS | LEAF RUST | GRAY MOLD | DOWN MDEW | LEAF SPOT | APPL SCAB | LEAF BLOT |
|---|---|---|---|---|---|---|---|---|
| 238 | − | − | − | − | − | 0 | 0 | 0 |
| 239 | − | − | − | − | − | 0 | 0 | 0 |
| 240 | − | − | − | − | − | 0 | 0 | 0 |
| 241 | − | − | − | − | − | 0 | 0 | 0 |
| 242 | + | + | + | − | + | − | + | − |
| 243 | + | ++ | + | − | ++ | 0 | 0 | 0 |
| 244 | − | − | − | − | − | 0 | 0 | 0 |
| 245 | − | − | − | − | − | 0 | 0 | 0 |
| 246 | + | − | − | − | ++ | 0 | 0 | 0 |
| 247 | − | − | − | − | − | 0 | 0 | 0 |
| 248 | + | − | − | − | − | 0 | 0 | 0 |
| 249 | − | − | − | − | − | 0 | 0 | 0 |
| 250 | − | − | − | − | − | 0 | 0 | 0 |
| 251 | − | − | + | 0 | − | 0 | 0 | 0 |
| 252 | − | + | + | − | + | 0 | 0 | 0 |
| 253 | − | − | + | − | + | 0 | 0 | 0 |
| 254 | − | − | − | − | − | 0 | 0 | 0 |

Additional Plant Pathology Tests

Selected compounds were further tested in the greenhouse against various pathogens. The compounds were formulated and applied as foliar sprays as in Test 1. Results are reported in the following Tables 7-9 using the rating scale of Table 6.

The following abbreviations are used in the Tables:

| | |
|---|---|
| PMW | = Wheat Powdery Mildew |
| PMB | = Barley Powdery Mildew |
| PMG | = Grape Powdery Mildew |
| PMC | = Cucumber Powdery Mildew |
| PMA | = Apple Powdery Mildew |
| BG | = Grape Botrytis |
| BT | = Tomato Botrytis |
| BB | = Bean Botrytis |
| DMG | = Grape Downy Mildew |
| LRW | = Wheat Leaf Rust |
| LS | = Wheat Leaf Spot |
| LB | = Wheat Leaf Blot |
| AS | = Apple Scab |
| TB | = Tomato Blight |
| PCH | = *Pseudocercosporella herpotuchoides* |

TABLE 7

| COMPOUND EX NO. | PMW | PMB | PMG | PMC | PMA |
|---|---|---|---|---|---|
| 1 | 0 | 0 | 0 | 0 | +++ |
| 2 | +++ | ++ | +++ | +++ | +++ |
| 4 | +++ | 0 | 0 | 0 | 0 |
| 6 | ++ | 0 | 0 | 0 | 0 |
| 8 | +++ | 0 | 0 | 0 | 0 |
| 9 | +++ | 0 | 0 | 0 | 0 |
| 12 | − | 0 | 0 | 0 | 0 |
| 14 | +++ | 0 | 0 | 0 | ++ |
| 16 | ++ | 0 | 0 | 0 | 0 |
| 17 | +++ | 0 | 0 | 0 | 0 |
| 18 | +++ | 0 | 0 | 0 | 0 |
| 20 | +++ | 0 | 0 | 0 | 0 |
| 21 | +++ | 0 | 0 | 0 | 0 |
| 24 | +++ | 0 | 0 | 0 | 0 |
| 28 | +++ | +++ | 0 | ++ | +++ |
| 35 | ++ | 0 | 0 | 0 | 0 |
| 36 | +++ | 0 | 0 | 0 | 0 |
| 52 | +++ | 0 | 0 | 0 | 0 |
| 58 | +++ | 0 | 0 | 0 | ++ |
| 60 | +++ | + | 0 | + | ++ |
| 62 | +++ | 0 | 0 | 0 | 0 |
| 75 | +++ | 0 | 0 | 0 | 0 |
| 77 | − | 0 | 0 | 0 | 0 |
| 82 | +++ | 0 | 0 | 0 | 0 |
| 85 | +++ | 0 | 0 | 0 | 0 |
| 86 | +++ | 0 | 0 | 0 | 0 |
| 88 | ++ | 0 | 0 | 0 | 0 |
| 89 | +++ | 0 | 0 | 0 | 0 |
| 90 | +++ | 0 | 0 | 0 | 0 |
| 91 | ++ | 0 | 0 | 0 | 0 |
| 113 | +++ | 0 | 0 | 0 | 0 |
| 126 | +++ | 0 | 0 | 0 | 0 |
| 145 | ++ | 0 | 0 | 0 | 0 |
| 161 | − | 0 | 0 | 0 | 0 |
| 185 | +++ | 0 | 0 | 0 | 0 |
| 220 | ++ | 0 | 0 | 0 | 0 |
| 234 | + | 0 | 0 | 0 | 0 |
| 244 | − | 0 | 0 | 0 | 0 |

TABLE 8

| COMPOUND EX NO. | BG | BT | BB | DMG | LRW |
|---|---|---|---|---|---|
| 2 | 0 | 0 | 0 | + | + |
| 28 | 0 | 0 | 0 | 0 | + |
| 31 | +++ | ++ | + | ++ | 0 |
| 32 | 0 | − | 0 | 0 | 0 |
| 33 | − | +++ | 0 | 0 | 0 |
| 34 | 0 | ++ | 0 | 0 | 0 |
| 35 | +++ | +++ | 0 | 0 | 0 |
| 58 | 0 | 0 | 0 | 0 | − |
| 60 | 0 | 0 | 0 | 0 | − |
| 78 | 0 | 0 | 0 | ++ | 0 |
| 91 | 0 | 0 | 0 | ++ | +++ |
| 98 | 0 | +++ | 0 | 0 | 0 |
| 118 | 0 | 0 | 0 | +++ | 0 |
| 119 | 0 | 0 | 0 | ++ | 0 |
| 152 | 0 | + | 0 | 0 | 0 |
| 162 | 0 | − | 0 | 0 | 0 |
| 179 | 0 | + | 0 | 0 | 0 |
| 234 | 0 | ++ | 0 | 0 | 0 |

TABLE 9

| COMPOUND EX NO. | LS | LB | AS | TB | PCH |
|---|---|---|---|---|---|
| 2 | 0 | + | 0 | 0 | 0 |
| 6 | + | 0 | 0 | 0 | 0 |
| 28 | 0 | 0 | 0 | 0 | + |
| 35 | + | 0 | +++ | + | 0 |
| 91 | 0 | 0 | 0 | ++ | 0 |
| 113 | 0 | 0 | 0 | 0 | ++ |
| 118 | 0 | 0 | 0 | + | 0 |

TABLE 9-continued

| COMPOUND EX NO. | LS | LB | AS | TB | PCH |
|---|---|---|---|---|---|
| 119 | 0 | 0 | 0 | + + | 0 |

Seed Treatment

The compound of Example 28 was tested as a seed coat treatment and was found to afford both wheat and barley plants excellent protection against powdery mildew when applied at rates between 0.1 and 6.4 g/kg.

Combinations

Fungal disease pathogens are known to develop resistance to fungicides. When strains resistant to a fungicide do develop, it becomes necessary to apply larger and larger amounts of the fungicide to obtain desired results. To retard the development of resistance to new fungicides, it is desirable to apply the new fungicides in combination with other fungicides. Use of a combination product also permits the product's spectrum of activity to be adjusted.

Accordingly, another aspect of the invention is a fungicidal combination comprising at least 1% by weight of a compound of formula (1) in combination with a second fungicide.

Contemplated classes of fungicides from which the second fungicide may be selected include:

1) N-substituted azoles, for example propiconazole, triademefon, flusilazol, diniconazole, ethyltrianol, myclobutanil, and prochloraz;

2) pyrimidines, such as fenarimol and nuarimol;

3) morpholines, such as fenpropimorph and tridemorph;

4) piperazines, such as triforine; and 5) pyridines, such as pyrifenox. Fungicides in these five classes all function by inhibiting sterol biosynthesis. Additional classes of contemplated fungicides, which have other mechanisms of action, include:

6) dithiocarbamates, such as maneb and mancozeb;

7) phthalimides, such as captafol;

8) isophthalonitrites, such as chlorothalonil;

9) dicarboximides, such as iprodione;

10) benzimidazoles, such as benomyl and carbendazim;

11) 2-aminopyrimidines, such as ethirimol;

12) carboxamides, such as carboxin; and 13) dinitrophenols, such as dinocap.

The fungicide combinations of the invention contain at least 1%, ordinarily 20 to 80%, and more typically 50 to 75% by weight of a compound of formula (1).

Certain combinations within the invention have been found to provide synergistic activity against a number of fungal pathogens. Synergism against powdery mildew and rust has been observed not only in greenhouse tests, but also under field conditions.

More specifically, synergism has been observed for certain combinations in which the second fungicide component was nuarimol, benomyl, chlorothalonil, prochloraz, propiconazole, triademefon, or tridemorph. The compounds of Examples 2, 14, 28, 35, and 60 were tested in such combinations. In general, it is believed that synergism can be expected under appropriate conditions from combinations comprising a compound of the formula (1) in combination with a sterol inhibiting fungicide of the type that inhibits C-14 demethylation; but, as evidenced by the foregoing list, synergism has also been observed with other classes of fungicides.

When it is stated that a composition displays synergism, we mean that the percent control of disease observed in a test of the composition exceeds the value predicted by the equation $$E = X + Y - \frac{XY}{100}$$

where X is the percent control observed in a test of component A applied at rate p, Y is the percent control observed in a test of component B applied at rate q, and E is the expected percent control for the combination of A+B applied at rate p+q. This test is based on an article by S. R. Colby, "Calculating Synergistic and Antagonistic Responses of Herbicide Combinations" Weeds, vol. 15, 20–22 (1967). The test operates on the theory that if components A and B each independently kill 50% of disease organisms, then, if used together, after A kills 50% of disease organisms, the best B can be expected to do is kill 50% of the remaining organisms, for an expected total of 75% control.

A given fungicidal composition may display synergism under certain conditions and not under others. Factors significant in determining whether synergism is displayed include, for example, the application rate, the timing of the application, and the genetic resistance of disease organisms to a component of the composition. When a combination is applied at a rate such that the applied amount of one component alone would afford nearly complete control of the organism, there is little room for improvement, and the synergistic potential of the combination may not be apparent. In regard to timing, if an application of fungicide is made before the fungal disease organism is well established, the organism is more susceptible, and there is less opportunity to show synergistic potential than in the case where the disease organism is well established. On the other hand, if a disease organism is genetically resistant to one component of a combination, so that the applied amount of the one component alone would afford little control of that particular organism, there is more opportunity for the combination to show synergism against that organism than in a case where a similar application rate is used against a non-resistant disease organism.

MITE/INSECT SCREEN

The compounds of Examples 1–254 were tested for miticidal and insecticidal activity in the following mite-/insect screen.

Each test compound was formulated by dissolving the compound in acetone/alcohol (50:50) mixture containing 23 g of "Toximul R" (sulfonate/nonionic surfactant blend) and 13 g of "Toximul S" (sulfonate/nonionic surfactant blend) per liter. These mixtures were then diluted with water to give the indicated concentrations.

Twospotted spider mites (*Tetranychus urticae* Koch) and melon aphids (*Aphis gossypii* Glover) were introduced on squash cotyledons and allowed to establish on both leaf surfaces. Other plants in the same treatment pot were left uninfested. The leaves were then sprayed with 5 ml of test solution using a DeVilbiss atomizing sprayer at 10 psi. Both surfaces of the leaves were covered until runoff, and then allowed to dry for one hour. Two uninfested leaves were then excised and placed into a Petri dish containing southern armyworm (*Spodopetra eridania* Cramer).

Activity on Southern corn rootworm (*Diabrotica undecimpuctata howardi* Barber) was evaluated by adding two ml of tap water, a presoaked corn seed, and 15 g of dry sandy soil to a one ounce plastic container. The soil was treated with 1 mL of test solution containing a predetermined concentration of test compound. After six to 12 hours of drying, five 2-3 instar corn rootworm larvae were added to the individual cups, which were then capped and held at 23° C.

After standard exposure periods, percent mortality and phytotoxicity were evaluated. Results for the compounds found to be active are reported in Table 11. The remaining compounds showed no activity. The following abbreviations are used in Table 10:

CRW refers to corn rootworm
SAW refers to Southern armyworm
SM refers to twospotted spider mites
MA refers to melon aphids.

pared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide ad-

TABLE 10

| EXAMPLE NUMBER | CRW RATE PPM | CRW RESULTS % | SAW SM & MA RATE PPM | SAW RESULTS % | SM RESULTS % | MA RESULTS % |
|---|---|---|---|---|---|---|
| 2 | 12.00 | 0 | 200 | 0 | 0 | 10 |
| 12 | 24.00 | 0 | 400 | 0 | 90 | 0 |
|  | 12.00 | 0 | 200 | 0 | 40 | 0 |
| 21 | 24.00 | 0 | 400 | 0 | 40 | 50 |
| 48 | 24.00 | 0 | 400 | 0 | 70 | 60 |
| 83 | 24.00 | 0 | 400 | 0 | 0 | 80 |
|  | 12.00 | 0 | 200 | 0 | 0 | 0 |
| 94 | 24.00 | 100 | 400 | 0 | 0 | 0 |
|  | 12.00 | 0 | 200 | 0 | 0 | 0 |
| 108 | 24.00 | 100 | 400 | 0 | 0 | 0 |
|  | 12.00 | 0 | 200 | 0 | 0 | 0 |
| 122 | 12.00 | 100 | 200 | 0 | 0 | 0 |
|  | 12.00 | 100 | 200 | 100 | 0 | 0 |
| 150 | 24.00 | 100 | 400 | 0 | 0 | 0 |
|  | 12.00 | 0 | 200 | 0 | 0 | 80 |
| 155 | 24.00 | 100 | 400 | 0 | 90 | 90 |
|  | 12.00 | 100 | 200 | 0 | 0 | 0 |
| 163 | 12.00 | 0 | 200 | 0 | 30 | 0 |
| 167 | 24.00 | 0 | 400 | 0 | 80 | 80 |
| 176 | 24.00 | 0 | 400 | 100 | 0 | 0 |
|  | 12.00 | 60 | 200 | 0 | 0 | 0 |
| 191 | 24.00 | 0 | 400 | 80 | 0 | 0 |
|  | 12.00 | 0 | 200 | 0 | 0 | 0 |
| 202 | 24.00 | 0 | 400 | 0 | 0 | 0 |
|  | 12.00 | 0 | 200 | 0 | 0 | 80 |
| 214 | 24.00 | 80 | 400 | 0 | 0 | 0 |
|  | 12.00 | 0 | 200 | 0 | 0 | 0 |
| 243 | 24.00 | 100 | 400 | 0 | 0 | 0 |
|  | 12.00 | 0 | 200 | 0 | 0 | 80 |
| 253 | 24.00 | 0 | 400 | 60 | 0 | 0 |
|  | 12.00 | 0 | 200 | 0 | 0 | 0 |

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions preducts of alkyl phenols.

Emulsifiable concentrates of the compounds comprise a convenient concentration of a compound, such as from about 10% to about 50% by weight of liquid, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants such as those mentioned above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

The following formulations of compounds of the invention have been prepared, and are typical of compositions useful in the practice of the present invention.

| A. Emulsifiable Concentrate | |
|---|---|
| 7-chloro-4-(4-fluorophenoxy)quinoline | 12.50% |
| "TOXIMUL D" | 1.75% |
| (nonionic/anionic surfactant blend) | |
| "TOXIMUL H" | 3.25% |
| (nonionic/anionic surfactant blend) | |
| "PANASOL AN3N" | 64.50% |
| (naphthalenic solvent) | |
| "DOWANOL PM" | 18.00% |
| (propyleneglycol methyl ether) | |
| B. Dry Flowable | |
| 7-chloro-4-(4-fluorophenoxy)quinoline | 18.13% |
| "STEPANOL M.E." (anionic surfactant) | 2.50% |
| gum arabic | 0.50% |
| "SELLOGEN HR" | 3.00% |
| (anionic dispersant and wetting agent) | |
| "HISIL 233" | 3.00% |
| (silica carrier) | |
| "POLYFON H" | 4.00% |
| (lignosulfonate dispersing agent) | |
| Barden clay | 8.87% |
| C. Wettable Powder | |
| 7-chloro-4-(4-fluorophenoxy)quinoline | 78.125% |
| "STEPANOL M.E." | 5.000% |
| "HISIL 233" | 5.000% |
| "POLYFON H" | 5.000% |
| Barden clay | 6.875% |
| D. Aqueous Suspension | |
| 7-chloro-4-(4-fluorophenoxy)quinoline | 12.5% |
| "MAKON 10" | 1.0% |
| (10 moles of ethyleneoxide nonyl phenol surfactant) | |
| "ZEOSYL 200" (silica) | 1.0% |
| "POLYFON H" | 0.2% |
| "AF-100" | 0.2% |
| (silicon based antifoam agent) | |
| 2% xanthan gum solution | 10.0% |
| tap water | 75.1% |
| E. Aqueous Suspension | |
| 5,7-dichloro-4-(4-fluorophenoxy)quinoline | 12.5% |
| "MAKON 10" | 1.0% |
| "ZEOSYL 200" | 1.0% |
| "AF-100" | 0.2% |
| "POLYFON H" | 0.2% |
| 2% xanthan gum solution | 10.0% |
| tap water | 75.1% |
| F. Aqueous Suspension | |
| 5,7-dichloro-4-(4-fluorophenoxy)quinoline | 12.5% |
| "TOXIMUL D" | 2.0% |
| "TOXIMUL H" | 2.0% |
| "EXXON 200" (naphthalenic solvent) | 83.5% |
| G. Emulsifiable Concentrate | |
| 8-chloro-4-(2-chlorophenoxy)quinoline | 17.8% |
| "TOXIMUL D" | 2.5% |
| "TOXIMUL H" | 2.5% |
| "EXXON 200" | 77.2% |
| H. Emulsifiable Concentrate | |
| 8-chloro-4-(2-chlorophenoxy)quinoline | 12.5% |
| "TOXIMUL D" | 2.5% |
| "TOXIMUL H" | 2.5% |
| "EXXON 200" | 82.5% |
| I. Emulsifiable Concentrate | |
| 8-chloro-4-(2-chloro-4-fluorophenoxy)-quinoline | 17.6% |
| "TOXIMUL D" | 2.5% |
| "TOXIMUL H" | 2.5% |
| "EXXON 200" | 77.4% |
| J. Emulsifiable Concentrate | |
| 8-chloro-4-(2-chloro-4-fluorophenoxy)-quinoline | 12.5% |
| "TOXIMUL D" | 2.5% |
| "TOXIMUL H" | 2.5% |
| "EXXON 200" | 82.5% |
| K. Emulsifiable Concentrate | |
| 5,7-dichloro-4-(4-fluorophenoxy)quinoline | 12.5% |
| "TOXIMUL D" | 2.0% |
| "TOXIMUL H" | 2.0% |
| "EXXON 200" | 83.5% |
| L. Wettable Powder | |
| 8-chloro-4-(2-chloro-4-fluorophenoxy)-quinoline | 25.8% |
| "SELLOGEN HR" | 5.0% |
| "POLYFON H" | 4.0% |
| "STEPANOL ME DRY" | 2.0% |
| "HISIL 233" | 3.0% |
| Barden clay | 60.2% |

We claim:

1. A fungicidal composition wherein the active ingredients comprise, in a fungicidally effective combination, a first fungicide and a second fungicide, the first fungicide being a compound of the formula (1)

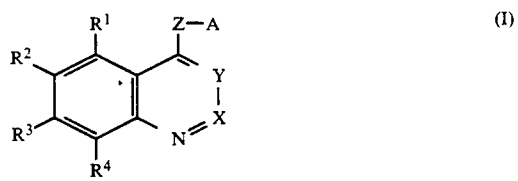

wherein

X is $CR^5$ or N, where $R^5$ is H, Cl or $CH_3$;

Y is $CR^{5'}$ where $R^{5'}$ is H, Cl, or Br;

Z is O, S, SO, $SO_2$, $NR^6$, where $R^6$ is H, $(C_1-C_4)$ alkyl, or $(C_1-C_4)$ alkanoyl, or $CR^7R^8$, where $R^7$ and $R^8$ are independently H, $(C_1-C_4)$ alkanoyl, ($C_1$-$C_4$) alkyl, ($C_1$-$C_4$) alkenyl, ($C_2$-$C_4$) alkynyl, CN, or OH, or $R^7$ and $R^8$ combine to form a carbocyclic ring containing four to six carbon atoms;

$R^1$ and $R^3$ are independently halo or $CH_3$ and $R^2$ and $R^4$ are H; or $R^3$ is halo, $R^1$ is halo or H, and $R^2$ and $R^4$ are H; or $R^4$ is halo and $R^1$ to $R^3$ are H;

A is
(a) a $C_1$-$C_{18}$ saturated or unsaturated hydrocarbon chain, straight chain or branched, optionally including a heteroatom selected from O, S, SO, or $SO_2$, and optionally substituted with halo, halo($C_1$-$C_4$) alkoxy, hydroxy, or ($C_1$-$C_4$) alkanoyl;
(b) ($C_3$-$C_8$) cycloalkyl or cycloalkenyl;
(c) a phenyl group of the formula (2)

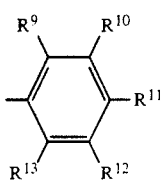

(2)

wherein $R^9$ to $R^{13}$ are independently
H,
CN,
$NO_2$,
OH,
halo,
($C_1$-$C_4$) alkyl,
($C_3$-$C_4$) branched alkyl,
($C_2$-$C_4$) alkanoyl,
halo ($C_1$-$C_7$) alkyl,
hydroxy ($C_1$-$C_7$) alkyl,
($C_1$-$C_7$) alkoxy,
halo ($C_1$-$C_7$) alkoxy,
($C_1$-$C_7$) alkylthio,
halo ($C_1$-$C_7$) alkylthio,
phenyl,
substituted phenyl,
phenoxy,
substituted phenoxy,
phenylthio,
substituted phenylthio,
phenyl ($C_1$-$C_4$) alkyl,
substituted phenyl ($C_1$-$C_4$) alkyl,
benzoyl,
$SiR^{20}R^{21}R^{22}$ or $OSiR^{20}R^{21}R^{22}$ where $R^{20}$, $R^{21}$, and $R^{22}$ are H, a $C_1$-$C_6$ alkyl group, straight chain or branched, phenyl, or substituted phenyl, provided that at least one of $R^{20}$, $R^{21}$, and $R^{22}$ is other than H, or $R^{11}$ and $R^{12}$ or $R^{12}$ and $R^{13}$ combine to form a carbocyclic ring, provided that unless all of $R^9$ to $R^{13}$ are H or F, then at least two of $R^9$ to $R^{13}$ are H;
(d) a furyl group of formula (3)

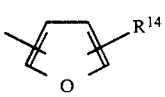

(3)

wherein $R^{14}$ is H, halo, halomethyl, CN, $NO_2$, ($C_1$-$C_4$) alkyl, ($C_3$-$C_4$) branched alkyl, phenyl, or ($C_1$-$C_4$) alkoxy,
(e) a thienyl group of formula (4)

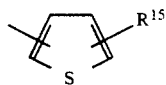

(4)

wherein $R^{15}$ is H, halo, halomethyl, CN, $NO_2$, ($C_1$-$C_4$) alkyl, ($C_3$-$C_4$) branched alkyl, phenyl, or ($C_1$-$C_4$) alkoxy;
(f) a group of formula (5) or (5a)

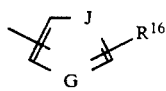

(5)

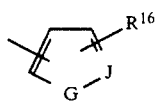

(5a)

wherein $R^{16}$ is H, halo, halomethyl, CN, $NO_2$, ($C_1$-$C_4$) alkyl, ($C_3$-$C_4$) branched alkyl, phenyl, substituted phenyl, or ($C_1$-$C_4$) alkoxy, and J is N or CH and G is O, $NR^{19}$ or CH, provided that either J is N or G is $NR^{19}$, where $R^{19}$ is H, ($C_1$-$C_4$) alkyl, ($C_1$-$C_4$) alkanoyl, phenylsulfonyl, or substituted phenylsulfonyl;
(g) a group selected from
1-naphthyl,
4-pyrazolyl,
3-methyl-4-pyrazolyl,
1,3-benzodioxolyl,
tricyclo[3.3.1.1(3,7)]dec-2-yl,
1-(3-chlorophenyl)-1H-tetrazol-5-yl,
pyridyl, and
pyridazinyl;
where, in the foregoing definitions, the term substituted phenyl refers to phenyl substituted with up to three groups selected from halo, ($C_1$-$C_{10}$) alkyl, branched ($C_3$-$C_6$) alkyl, halo ($C_1$-$C_7$) alkyl, hydroxy ($C_1$-$C_7$)alkyl, ($C_1$-$C_7$) alkoxy, halo ($C_1$-$C_7$) alkoxy, phenoxy, phenyl, $NO_2$, OH, CN ($C_1$-$C_4$) alkanoyloxy, or benzyloxy;
the term substituted phenoxy refers to a phenoxy group substituted with up to three groups selected from halo, ($C_1$-$C_{10}$) alkyl, branched ($C_3$-$C_6$) alkyl, halo ($C_1$-$C_7$) alkyl, hydroxy ($C_1$-$C_7$) alkyl, ($C_1$-$C_7$) alkoxy, halo ($C_1$-$C_7$) alkoxy, phenoxy, phenyl, $NO_2$, OH, CN ($C_1$-$C_4$) alkanoyloxy, or benzyloxy;
the term substituted phenylthio refers to a phenylthio group substituted with up to three groups selected from halo, ($C_1$-$C_{10}$) alkyl, branched ($C_3$-$C_6$) alkyl, halo ($C_1$-$C_7$) alkyl, hydroxy ($C_1$-$C_7$) alkyl, ($C_1$-$C_7$) alkoxy, halo ($C_1$-$C_7$) alkoxy, phenoxy, phenyl, $NO_2$, OH, CN ($C_1$-$C_4$) alkanoyloxy, or benzyloxy; and
the term substituted phenylsulfonyl refers to a phenylsulfonyl group substituted with up to three groups selected from halo, ($C_1$-$C_{10}$) alkyl, branched ($C_3$-$C_6$) alkyl, halo ($C_1$-$C_7$) alkyl, hydroxy ($C_1$-$C_7$) alkyl, ($C_1$-$C_7$) alkoxy, halo ($C_1$-$C_7$) alkoxy, phenoxy, phenyl, $NO_2$, OH, CN ($C_1$-$C_4$) alkanoyloxy, or benzyloxy;
or an acid addition salt of a compound of formula (1) or an N-oxide of a compound of formula (1) where Y is CH; provided Z is $CR^7R^8$ if A is a group described in paragraph (d), (e), or (f); and provided that Z is S, SO, or SO$_2$ if A is a group described in paragraph (a);

provided that the first and second fungicide are each present in an amount that contributes to the fungicidal activity of the composition.

2. A composition of claim 1 wherein the first fungicide is a compound of formula (1) wherein R$^3$ is Cl and the rest of R$^1$ to R$^4$ are H.

3. A composition of claim 1 wherein the first fungicide is a compound of formula (1) wherein R$^1$ and R$^3$ are Cl and R$^2$ and R$^4$ are H.

4. A composition of claim 1 wherein the first fungicide is a compound of formula (1) wherein X and Y are CH.

5. A composition of claim 1 wherein the first fungicide is a compound of formula (1) wherein Z is O.

6. A composition of claim 5 wherein the first fungicide is a compound of formula (1) wherein R$^1$ and R$^3$ are Cl and R$^2$ and R$^4$ are H.

7. A composition of claim 5 wherein the first fungicide is a compound of formula (1) wherein R$^3$ is Cl and R$^1$, R$^2$, and R$^4$ are H.

8. A composition of claim 1 wherein the first fungicide is a compound of formula (1) wherein R$^3$ is Br and R$^1$, R$^2$, and R$^4$ are H.

9. A composition of claim 1 wherein the first fungicide is a compound of formula (1) wherein R$^4$ is Cl and R$^1$ to R$^3$ are H.

10. A composition of claim 1 wherein the first fungicide is a compound of formula (1) wherein A is substituted or unsubstituted phenyl.

11. A composition of claim 1 wherein the first fungicide is a compound of formula (1) wherein A is 4-fluorophenyl, 2-chlorophenyl, 2-chloro-4-fluorophenyl.

12. A composition of claim 1 wherein the first fungicide is a compound of formula (1) wherein A is phenyl ortho-substituted with a group selected from halo, CF$_3$, CN, or NO$_2$.

13. A composition of claim 1 wherein the first fungicide is 5,7-dichloro-4-(4-fluorophenoxy)quinoline, or the 1-oxide thereof.

14. A composition of claim 1 wherein the first fungicide is 7-chloro-4-[2-(trifluoromethyl)phenoxy]quinoline, or the 1-oxide, thereof.

15. A composition of claim 1 wherein the first fungicide is 5,7-dichloro-4-phenoxyquinoline, or the 1-oxide thereof.

16. A composition of claim 1 wherein the first fungicide is 7-chloro-4-(2-nitrophenoxy)-quinoline, or the 1-oxide thereof.

17. A composition of claim 1 wherein the second fungicide is an inhibitor of sterol biosynthesis.

18. A composition of claim 1 wherein the second fungicide is an N-substituted azole selected from propiconazole, triademefon, flusilazol, diniconazole, ethyltrianol, myclobutanil, and prochloraz.

19. A composition of claim 1 wherein the second fungicide is fenpropimorph or tridemorph.

20. A composition of claim 1 wherein the second fungicide is selected from the group consisting of nuarimol, benomyl, chlorothalonil, prochloraz, propiconazole, triademefon, and tridemorph.

21. A composition of claim 1 wherein the combination of first and second fungicides consists of 20-80% by weight of a compound of formula (1) and the balance is the second fungicide.

* * * * *